United States Patent
Li et al.

(10) Patent No.: US 10,233,166 B2
(45) Date of Patent: Mar. 19, 2019

(54) ALKYLENE OXIDE SEPARATION SYSTEMS, METHODS, AND APPARATUSES

(71) Applicant: Lyondell Chemical Technology, L.P., Houston, TX (US)

(72) Inventors: Xiangmin Li, Mendham, NJ (US); Te Chang, Houston, TX (US); David W. Leyshon, Houston, TX (US); Walter S. Dubner, Wilmington, DE (US); Elizabeth I. Ross-Medgaarden, Humble, TX (US)

(73) Assignee: Lyondell Chemical Technology, L.P., Houston, TX (US)

(*) Notice: Subject to any disclaimer, the term of this patent is extended or adjusted under 35 U.S.C. 154(b) by 139 days.

(21) Appl. No.: 15/419,713

(22) Filed: Jan. 30, 2017

(65) Prior Publication Data

US 2017/0137394 A1 May 18, 2017

Related U.S. Application Data

(62) Division of application No. 14/336,149, filed on Jul. 21, 2014, now Pat. No. 9,593,090.

(Continued)

(51) Int. Cl.
*C07D 301/32* (2006.01)
*B01D 3/14* (2006.01)
(Continued)

(52) U.S. Cl.
CPC ........... *C07D 301/32* (2013.01); *B01D 3/143* (2013.01); *B01D 11/0488* (2013.01); *B01D 11/0492* (2013.01); *B01D 17/0214* (2013.01)

(58) Field of Classification Search
CPC .............................. C07D 301/32; B01D 3/143
See application file for complete search history.

(56) References Cited

U.S. PATENT DOCUMENTS

| 2,194,851 A | 3/1940 | Guinot |
| 2,610,141 A | 9/1952 | Drout |

(Continued)

FOREIGN PATENT DOCUMENTS

| EP | 1816129 A1 | 8/2007 |
| WO | WO-2004083196 A1 | 9/2004 |
| WO | WO-2012170685 A1 | 12/2012 |

OTHER PUBLICATIONS

The International Search Report and Written Opinion for PCT/US2014/048436 dated Nov. 13, 2014.
(Continued)

*Primary Examiner* — Jonathan Miller

(57) ABSTRACT

A propylene oxide separation system that comprises a distillation column, a decanter, and water wash system. The distillation column is configured to receive a crude propylene oxide stream, discharge an impurity stream that comprises methanol and water, and discharge a bottoms stream that comprises a majority of the propylene oxide entering in the crude propylene oxide stream. The decanter is configured to receive at least a portion of the impurity stream and a hydrocarbon solvent to provide for formation in the decanter of an organic phase and an aqueous phase. The organic phase comprises propylene oxide and hydrocarbon solvent, and is sent to the distillation column. The aqueous phase comprises a majority weight percent of the methanol and the water entering in the impurity stream. The water wash system is configured to receive and purge the aqueous phase from the propylene oxide separation system.

4 Claims, 12 Drawing Sheets

Related U.S. Application Data

(60) Provisional application No. 61/859,549, filed on Jul. 29, 2013.

(51) Int. Cl.
   *B01D 17/02* (2006.01)
   *B01D 11/04* (2006.01)

(56) References Cited

U.S. PATENT DOCUMENTS

| | | |
|---|---|---|
| 2,622,060 A | 12/1952 | Robeson et al. |
| 3,287,234 A | 11/1966 | Steel et al. |
| 3,338,800 A | 8/1967 | Binning et al. |
| 3,632,482 A | 1/1972 | Hoory et al. |
| 3,642,614 A | 2/1972 | Van Tassell |
| 3,881,996 A | 5/1975 | Schmidt |
| 4,140,588 A | 2/1979 | Schmidt |
| 4,691,035 A | 9/1987 | Sanderson et al. |
| 4,775,475 A | 10/1988 | Johnson |
| 5,171,868 A | 12/1992 | Albal et al. |
| 7,666,299 B2 | 2/2010 | Wu et al. |
| 8,981,133 B2 | 3/2015 | Li et al. |
| 2002/0088704 A1 | 7/2002 | Laborie et al. |
| 2004/0106811 A1 | 6/2004 | Hofen et al. |
| 2005/0034970 A1 | 2/2005 | Schwarz et al. |
| 2006/0006054 A1 | 1/2006 | Gobbel et al. |
| 2006/0113180 A1 | 6/2006 | Patrascu et al. |
| 2008/0035468 A1 | 2/2008 | Nakayama et al. |
| 2010/0078391 A1 | 4/2010 | Lindsey et al. |
| 2012/0077996 A1 | 3/2012 | Sawyer |
| 2012/0312680 A1 | 12/2012 | Li et al. |

OTHER PUBLICATIONS

Supplementary European Search Report for EP Application No. 14832850.3 dated Nov. 29, 2016.
Intellectual Property Office of Singapore Search Report & Written Opinion for SG Application No. 11201600085R dated Jul. 29, 2016.

ALKYLENE OXIDE SEPARATION SYSTEMS, METHODS, AND APPARATUSES

CROSS-REFERENCE TO RELATED APPLICATIONS

This application is a divisional patent application of U.S. patent application Ser. No. 14/336,149, filed Jul. 21, 2014, which claims benefit and priority of U.S. Provisional Patent Application No. 61/859,549, filed on Jul. 29, 2013, the disclosures of which are incorporated herein by reference in their entirety.

FIELD OF THE INVENTION

The present invention relates to a process for the purification and recovery of propylene oxide which is formed from epoxidation of propylene with hydroperoxides derived from oxidation of isobutane, ethyl benzene or cumene. In particular, the process improves the separation of light aldehydes, such as formaldehyde and acetaldehyde, from propylene oxide.

BACKGROUND OF THE INVENTION

Approximately 14.5 billion pounds of propylene oxide are produced every year. Propylene oxide has many uses. Between 60 and 70% of all propylene oxide is converted to polyether polyols for the production of polyurethane plastics. About 20% of propylene oxide is hydrolyzed into propylene glycol, via a process which is accelerated either by thermal reaction or by acid or base catalysis. Other major products are polypropylene glycol, propylene glycols ethers, and propylene carbonate. To produce these end products, propylene oxide free of impurities is needed.

Methods of producing alkylene oxides including propylene oxide involve hydrochlorination and epoxidation of its corresponding olefins. The oxidates used in the epoxidation processes are derived from tertiary or secondary hydrocarbons by direct oxidation with molecular oxygen; hence, they contain oxygenate impurities and precursors. Additional oxygenate impurities are also generated in the step of epoxidation of olefins. Crude alkylene oxides, such as propylene oxide, particularly those produced from epoxidation with hydrocarbon oxidates contain a significant amount of oxygenated impurities difficult to separate from alkylene oxides. The impurities generally include water, acids, alcohols, aldehydes, ketones and esters. A need exists for continued improvement of systems and methods for separating propylene oxide from these impurity constituents of effluent streams of various methods of producing propylene oxide.

U.S. Pat. No. 3,338,800 teaches extractive distillation of alkylene oxides having from 3 to 18 carbon atoms with a paraffin or paraffin naphtha solvent. More particularly, this patent suggests that oxygenated impurities boiling within 5° C. of the alkylene oxide may be separated by extractive distillation using acyclic paraffinic hydrocarbons as solvents having boiling points at least 35° C. above the boiling points of the said impurities. The problem addressed by this patent is that epoxide fractions produced by the direct oxidation of ethylenically unsaturated compounds with molecular oxygen in the liquid phase contain oxygenated impurities which, because their boiling points are similar to the desired epoxide product, cannot be separated by conventional distillation techniques.

U.S. Pat. No. 3,881,996 teaches that the sequence of the fractionation steps has a major effect on the final purity of the propylene oxide obtained, particularly with regard to aldehyde content. Substantially improved results are obtained when the removal of acetaldehyde and lower boiling materials precedes the step in which propylene oxide is separated from propionaldehyde and higher boiling material. This result is highly unusual and is not in accord with customary calculable performance of fractional distillation equipment. The inventor believes that chemical reactions may be occurring during distillation which interfere with the normal mass transfer steps and thereby produce anomalous results. However, the scientific reasoning is not offered.

U.S. Pat. Nos. 3,464,897 and 3,843,488 teach using hydrocarbon solvents of 8-20 carbon atoms can effective remove C5-C7 impurities from propylene oxide in extractive distillation. U.S. Pat. No. 3,607,669 teaches a method for separating propylene oxide from water by distilling the mixture in the presence of acyclic or cyclic paraffin containing 8 to 12 carbon atoms by breaking water-propylene oxide azeotrope at elevated pressure. There are many other U.S. Patents, such as U.S. Pat. Nos. 4,140,588, 5,000,825, 5,006,206, 5,116,466, 5,116,467, 5,139,622, 5,145,561, 5,145,563, 5,154,803, 5,154,804, 5,160,587, 5,340,446, 5,620,568, 5,958,192 and 6,559,248 that reflect use of various solvents in extractive distillation operations for propylene oxide purification. U.S. Pat. Nos. 2,550,847, 2,622,060, 3,350,417, 3,477,919, 4,691,034, 4,691,035, 5,106,458 and 5,107,002 teach how to separate methyl formate from propylene oxide. Although these patents teach the removal of selected propylene oxide impurities, none address removal of aldehydes, particularly formaldehyde and acetaldehyde.

U.S. Pat. No. 6,024,840 uses methanol as extractive solvent to remove acetaldehyde from propylene. However, solvent methanol itself becomes close-boiling propylene oxide contaminant. U.S. Pat. No. 7,705,167 teaches using water wash propylene oxide followed by contacting aqueous phase with hydrocarbon extractive solvent and subsequent distillation. These teachings are impractical for the existing plant improvement. Because it is difficult to recover a propylene oxide containing total aldehydes below 50 ppm and free of formaldehyde, particularly for propylene oxide produced from tert-butyl hydroperoxide process, it is the objective of the present invention to provide a method applicable to the existing plants for recovering propylene oxide in a high state of purity low in aldehydes without substantial loss of propylene oxide product.

SUMMARY OF THE INVENTION

An aspect of the invention relates to propylene oxide separation system including: a distillation column configured to receive a crude propylene oxide stream, discharge an impurity stream having methanol and water, and discharge a bottoms stream having a majority of the propylene oxide entering in the crude propylene oxide stream; a decanter configured to receive the impurity stream and a hydrocarbon solvent to provide for formation in the decanter of an organic phase having propylene oxide and hydrocarbon solvent, and an aqueous phase comprising a majority weight percent of the methanol and the water entering in the impurity stream; and a water wash system configured to receive and purge the aqueous phase from the propylene oxide separation system, wherein the organic phase in the decanter is sent to the distillation column.

The crude propylene oxide stream may be a propylene oxide reactor effluent stream, such as in a propylene oxide/tert-Butanol process system. The distillation column may include an overhead condenser, and wherein the distillation column is configured with an overhead vapor purge of non-condensed components from the overhead condenser. The decanter maybe an overhead decanter to the distillation column, and receive the impurity stream from the overhead condenser. On the other hand, the decanter may be a side decanter to the distillation column, and receive the impurity stream from a liquid side draw of the distillation column. The distillation column may be a solvent-lights column. The water wash system may include a mixer, such as a static mixer, and a coalescer. Further, a solvent stripper may receive the bottoms stream from the distillation column, wherein the solvent stripper discharges a solvent-stripper overhead stream having a majority of the propylene oxide entering the solvent stripper in the bottoms stream from the distillation column, and discharges a solvent-stripper bottoms stream comprising at least a portion of the hydrocarbon solvent received at the decanter. Additionally an extraction column may subject the solvent-stripper overhead stream from the solvent stripper to a hydrocarbon solvent extraction to remove impurities, wherein the extraction column purges the removed impurities having formaldehyde to the water wash system Another aspect of the invention relates to a method for separating propylene oxide from a crude propylene oxide stream in a separation system, the method including: feeding the crude propylene oxide stream to a distillation column; discharging an impurity stream from the distillation column to a decanter, the impurity stream having methanol and water; feeding hydrocarbon solvent to the decanter; forming in the decanter an organic phase including propylene oxide and hydrocarbon solvent, and an aqueous phase having a majority weight percent of the methanol and the water fed to the decanter in the impurity stream; washing the aqueous phase with water and purging the washed aqueous phase from the separation system; and sending the organic phase to the distillation column.

The discharging of the impurity stream may include discharging the impurity stream to the decanter via an overhead condenser of the distillation column, and the method further including purging a vapor stream from the overhead condenser. On the other hand, the discharging the impurity stream may involve discharging the impurity stream to the decanter via a liquid side draw of the distillation column. The method may include: discharging a bottoms stream from the distillation column, the bottoms stream having a majority of the propylene oxide entering the distillation column in the crude propylene oxide stream; separating formaldehyde from the bottoms stream; and sending the formaldehyde to a water wash system performing the washing of the aqueous phase with water.

Yet another aspect of the invention relates to a propylene oxide separation system including: a distillation column configured to receive a processed crude propylene oxide stream, discharge an impurity stream comprising methanol and water, and discharge a bottoms stream having a majority of the propylene oxide entering in the processed crude propylene oxide stream; a mixer configured to mix caustic (e.g., is or having sodium hydroxide) with the impurity stream to give a caustic-treated impurity stream; and a backwash column configured to subject the caustic-treated impurity stream to both an aqueous extraction and an organic extraction.

The backwash column may purge an aqueous stream having a majority amount of the methanol and the water in the impurity stream. Also, the backwash column may discharge an organic stream (having hydrocarbon solvent and propylene oxide) to the distillation column. An extraction column may be disposed downstream of the distillation column, and purge formaldehyde to the mixer, wherein the formaldehyde is carryover from the bottoms stream of the distillation column.

The propylene oxide separation system may further include: a lights distillation column configured to receive a crude propylene oxide stream, remove light components, and discharge a lights-distillation column bottoms stream comprising a majority of the propylene oxide from the crude propylene oxide stream; and a heavies distillation column configured to receive the lights-distillation column bottoms stream, remove heavy components, and discharge an overhead stream comprising a majority of the propylene oxide from the lights-distillation column bottoms stream, and wherein the overhead stream is or a portion of the processed crude propylene oxide stream. Alternatively, the propylene oxide separation may include: a heavies distillation column configured to receive a crude propylene oxide stream, remove heavy components from the crude propylene oxide stream, and discharge an overhead stream comprising a majority of the propylene oxide from the crude propylene oxide stream; and a lights distillation column configured to receive the overhead stream, remove heavy components from the overhead stream, and discharge a lights-distillation column bottoms stream having a majority of the propylene oxide from the overhead stream, and wherein the lights-distillation column bottoms stream is or a portion of the processed crude propylene oxide stream.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

These and other features, aspects, and advantages of the present invention will become better understood with reference to the following description and appended claims, and accompanying drawings where:

Figure 1:
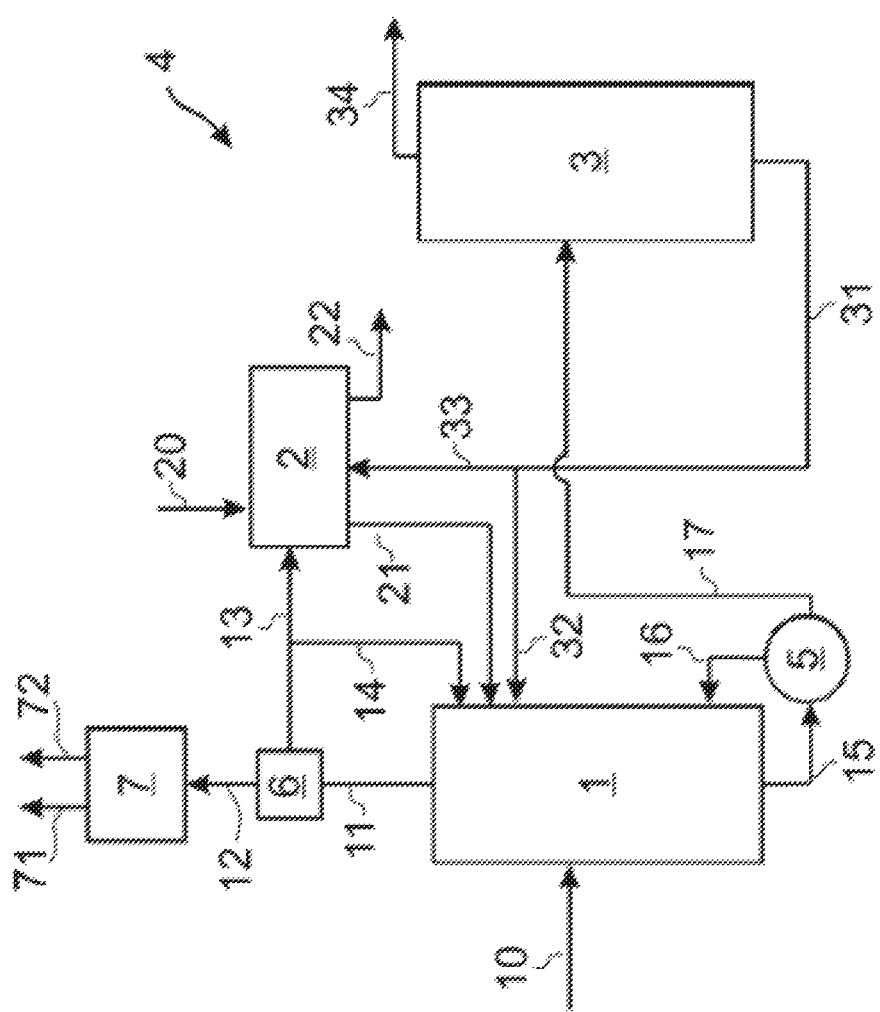
FIG. 1 is a schematic block diagram of a propylene oxide separation system according to one embodiment.

It should be understood that the various embodiments are not limited to the arrangements and instrumentality shown in the drawings.

DETAILED DESCRIPTION OF EMBODIMENTS OF THE INVENTION

The present disclosure may be understood more readily by reference to the following detailed description of preferred embodiments of the invention as well as to the examples included therein. Various streams are discussed throughout the present disclosure as containing impurities, which are identified below within the context of the particular stream. Although various streams may be identified below by more specific names, to the extent a stream is identified as containing impurities to be removed, such stream is also an impurity stream.

One method for producing propylene oxide (PO), also known as epoxypropane, propylene epoxide, 1,2-propylene oxide, methyl oxirane, 1,2-epoxypropane, propene oxide, methyl ethylene oxide, methylethylene oxide, will now be described. First, as shown in Scheme 1, isobutane (IB), also known as 2-methylpropane, can be reacted with oxygen to form tert-butyl hydroperoxide (TBHP), also known as 2-Methylpropane-2-peroxol.

Scheme 1

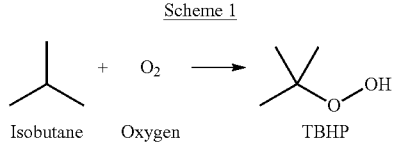

Isobutane   Oxygen   TBHP

Subsequently, as shown in Scheme 2, propylene, also known as propene, can be reacted with TBHP in the presence of a catalyst to form PO and tert-Butanol (TBA), also known as 2-methyl-2-propanol.

Scheme 2

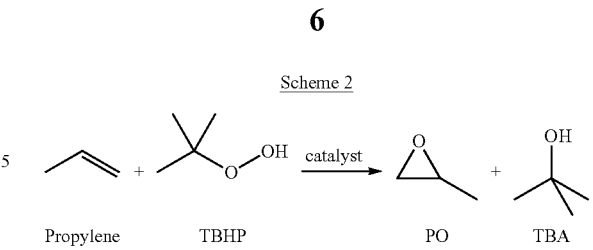

Propylene   TBHP   PO   TBA

Since this method produces both PO and TBA it shall be referred to as the PO/TBA process.

The PO/TBA process can also yield a variety of unwanted side products. Without wishing to be bound by theory, non-selective reactions can take place to produce the impurities. Such non-selective reactions can include, but are not limited to the reactions depicted in Schemes 3-6.

Scheme 3

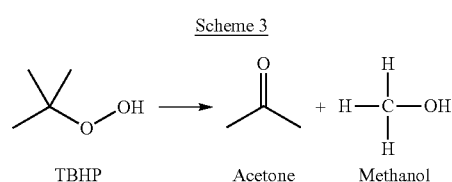

TBHP   Acetone   Methanol

Scheme 4

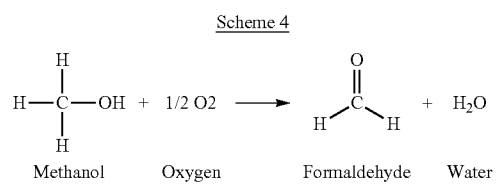

Methanol   Oxygen   Formaldehyde   Water

Scheme 5

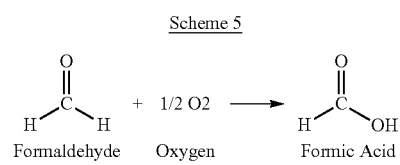

Formaldehyde   Oxygen   Formic Acid

Scheme 6

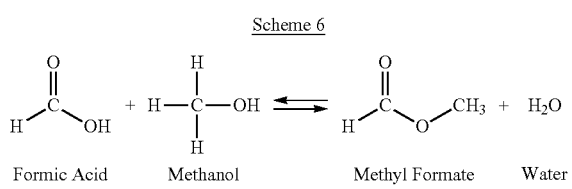

Formic Acid   Methanol   Methyl Formate   Water

Acetaldehyde can also be formed in the PO/TBA process. A possible mechanism for the formation of acetaldehyde is shown in Scheme 7.

Scheme 7

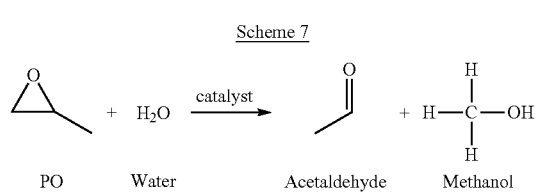

PO   Water   Acetaldehyde   Methanol

The concentrations of these impurities that end up in a crude PO stream from a PO/TBA process can vary.

Methyl formate can be present in an amount within a range having a lower limit and/or an upper limit, each expressed as a weight percentage of the total composition of a crude PO stream from a PO/TBA process. The range can include or exclude the lower limit and/or the upper limit. The methyl formate lower limit and/or upper limit can be selected from 0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 2, 3, 4, 5, and 10 weight percent. For example methyl formate can be present in an amount of greater than 0.06 weight percent of the total composition of a crude PO stream from a PO/TBA process.

Methanol can be present in an amount within a range having a lower limit and/or an upper limit, each expressed as a weight percentage of the total composition of a crude PO stream from a PO/TBA process. The range can include or exclude the lower limit and/or the upper limit. The methanol lower limit and/or upper limit can be selected from 0, 0.001, 0.002, 0.003, 0.0031, 0.0032, 0.0033, 0.0034, 0.0035, 0.0036, 0.0037, 0.0038, 0.0039, 0.0139, 0.0239, 0.0339, 0.0439, 0.0539, 0.0639, 0.0739, 0.0839, 0.0939, 0.1039, 0.1049, 0.1059, 0.1069, 0.1079, 0.1089, 0.1099, 0.1109, 0.1119, 0.1129, 0.1139, 0.1149, 0.1159, 0.116, 0.1161, 0.1162, 0.1163, 0.1164, 0.1165, 0.1166, 0.1167, 0.1168, 0.1169, 0.117, 0.1171, 0.1172, 0.1173, 0.1174, 0.1175, 0.1176, 0.1177, 0.2177, 0.3177, 0.4177, 0.5177, 0.6177, 0.7177, 0.8177, 0.9177, 1, 2, 3, 4, 5, and 10 weight percent. For example, methanol can be present in an amount greater than 0.0032 weight percent or in an amount greater than 0.1172 weight percent of the total composition of a crude PO stream from a PO/TBA process.

Acetaldehyde can be present in an amount within a range having a lower limit and/or an upper limit, each expressed as a weight percentage of the total composition of a crude PO stream from a PO/TBA process. The range can include or exclude the lower limit and/or the upper limit. The acetaldehyde lower limit and/or upper limit can be selected from 0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 2, 3, 4, 5, and 10 weight percent. For example, acetaldehyde can be present in an amount of greater than 0.03 weight percent of the total composition of a crude PO stream from a PO/TBA process.

Water can be present in an amount within a range having a lower limit and/or an upper limit, each expressed as a weight percentage of the total composition of a crude PO stream from a PO/TBA process. The range can include or exclude the lower limit and/or the upper limit. The water lower limit and/or upper limit can be selected from 0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 2, 3, 4, 5, and 10 weight percent. For example, water can be present in an amount of greater than 0.16 weight percent of the total composition of a crude PO stream from a PO/TBA process.

Formaldehyde can be present in an amount within a range having a lower limit and/or an upper limit, each expressed as a weight percentage of the total composition of a crude PO stream from a PO/TBA process. The range can include or exclude the lower limit and/or the upper limit. The formaldehyde lower limit and/or upper limit can be selected from 0, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 2, 3, 4, 5, and 10 weight percent. For example, formaldehyde can be present in an amount of greater than 0.005 weight percent of the total composition of a crude PO stream from a PO/TBA process.

Tables 1 and 2 show exemplary concentrations of key impurities in a crude PO stream from a PO/TBA process, each expressed as a weight percentage of the total composition of a crude PO stream from a PO/TBA process.

TABLE 1

| Component | Average weight percent |
| --- | --- |
| MeF | 0.06 |
| Methanol | 0.1172 |
| Acetaldehyde | 0.03 |
| Water | 0.16 |
| Formaldehyde | 0.005 |

TABLE 2

| Component | Average weight percent |
| --- | --- |
| MeF | 0.06 |
| Methanol | 0.0032 |
| Acetaldehyde | 0.03 |
| Water | 0.16 |
| Formaldehyde | 0.005 |

Without wishing to be bound by theory, a major problem is caused by the reaction of methanol with formaldehyde. As shown in Scheme 8, an aldehyde, like formaldehyde, can react with an alcohol, like methanol to form a hemiacetal. According to Scheme 8, R1 and R2 can be hydrogen, or a $C_{1-10}$ alkyl.

Scheme 8

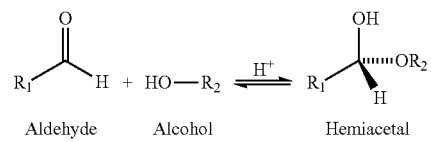

Aldehyde    Alcohol    Hemiacetal

Formation of an acetal can occur when the hydroxyl group of a hemiacetal becomes protonated and is lost as water, as illustrated in Scheme 9, wherein R1, R2, and R3 can be hydrogen, or a $C_{1-10}$ alkyl.

Scheme 9

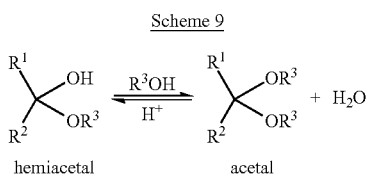

Both formaldehyde and methanol would be lights by themselves, but the formation of hemiacetals and acetals can make them heavy. Subsequently, these addition products can travel downstream where temperatures increase and the reaction reverses. When the reaction reverses, aldehydes can become trapped with the desired propylene oxide product.

Referring to FIG. 1, an embodiment of the present disclosure relates to a separation system 4 for removing impurities from a crude PO stream 10 from a PO/TBA process. The crude PO stream 10 can include, but is not limited to, all of the impurities described above along with the desired product, propylene oxide. The crude PO stream 10 can be fed into a distillation column, such as solvent-lights column 1. Most of the impurities (for example, methanol) in crude PO stream 10 can be removed in an overhead stream 11 and sent to a cooler system 6 (see also FIG. 2) which may provide for partial condensation. The remaining vapor stream 12 can be forwarded from the cooler system 6 to an overhead condenser system 7 (see also FIG. 2) to give a vapor purge stream 71 and a liquid purge stream 72, for example. All or some of the condensation exiting the cooler system 6 may be sent as a wash inlet stream 13 to a water wash apparatus 2, with a portion of the condensation optionally taken as reflux back to the solvent-lights column 1.

For instance, in the illustrated example of FIG. 1, a reflux stream 14 can be taken from wash inlet stream 13 and recycled to the solvent-lights column 1. Wash inlet stream 13 can be fed into the water wash apparatus 2. A water inlet stream 20 can also be fed into the water wash apparatus 2. Solvents recovered from the water wash apparatus 2 can be recycled via recycle stream 21 to the solvent-light column 1. An aqueous purge stream 22 can also be removed from the water wash apparatus 2.

The solvent-lights bottom product stream 15 of solvent-lights column 1 can be passed through a solvent-lights reboiler 5. A solvent-lights reboiler vapor stream 16 can be fed back to the solvent-lights column 1. A solvent-lights reboiler bottoms stream 17 can be added to solvent stripper column 3. An overhead product stream 34 of the solvent stripper column 3 can include the desired propylene oxide product. Overhead product stream 34 can be processed to achieve further separation of propylene oxide. A bottoms product stream 31 of the solvent stripper column 3 can be recycled to the water wash apparatus 2 via stream 33 and/or to the solvent-light column 1 via stream 32.

An embodiment of the solvent-lights column 1 is now described in greater detail. The solvent-lights column 1 can be made of any suitable material, including but not limited to carbon steel or stainless steel. The solvent-light column 1 can include any suitable number of trays or theoretical trays, for example, about 25 theoretical stages. In certain embodiments, crude PO stream 10 can be added at tray 11 to 15, counting from the bottom. A packing material can be employed in the solvent-lights column to enhance vapor-liquid contact. Suitable packing materials can be made from any material including glass, metal, plastic, and ceramic. The packing can be structured or dumped. Trays such as sieve trays, bubble cap trays or valve trays can also be used.

As described below, water wash apparatus 2 is effective in removing key light impurities such as methyl formate, formaldehyde, acetaldehyde, and methanol. This helps keep hemiacetal or acetal formation as low as possible in the solvent-lights column 1. As already discussed, hemiacetal and acetal could enter into the solvent-light bottom product stream 15 and later breakdown in downstream columns as aldehydes to contaminate the propylene oxide product.

Unexpected and beneficial results can be obtained by operating solvent-lights column 1 and/or solvent-lights reboiler 5 at a temperature within a range having a lower limit and/or an upper limit, each expressed in degrees Celsius. The range can include or exclude the lower limit and/or the upper limit. The reboiler temperature lower limit and/or upper limit can be selected from 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, and 160 degrees Celsius. For example, the solvent-lights reboiler 5 can be operated at a temperature of 114 degrees Celsius or in a range of from 80 to 120 degrees Celsius.

Additionally or alternatively, unexpectedly beneficial results can be obtained by operating solvent-lights column 1 at a pressure within a range having a lower limit and/or an upper limit, each expressed in psig. The range can include or exclude the lower limit and/or the upper limit. The pressure lower limit and/or upper limit can be selected from 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, and 60 psig. For example, the solvent-lights column 1 can be operated at a pressure of 30 psig or in a range of from 20 to 50 psig.

Without wishing to be bound by theory, it is believed that by operating solvent-lights reboiler 5 at temperatures and/or pressures in the above-recited ranges, heavies such as hemiacetal or acetal formed in solvent-lights column 1, can break down into aldehydes. These aldehydes can then be removed to the overhead of the solvent-lights column 1 and eventually be purged out via water wash apparatus 2 or via the remaining vapor stream 12 instead of staying in the column bottom and contaminating the PO product.

One embodiment of the present disclosure relates to a method for removing impurities from a crude PO stream 10 from a PO/TBA process. The crude PO stream 10 can have a composition as previously defined. The method can include passing the crude PO stream 10 through a distillation column, such as solvent-lights column 1. The distillation column can be operated at the temperatures and pressures as previously defined.

Vapor Liquid Equilibrium (VLE) studies confirm that at increased pressure or temperature, acetaldehyde relative volatility to PO decreases, which indicates a more difficult aldehyde separation in the solvent-light column 1 at a higher pressure when alcohols are not present. Unexpectedly, with alcohols present, higher temperature and pressure result in a greater relative volatility of acetaldehyde relative to PO than at a lower pressure. Results of the experimental VLE studies are given in Tables 3 and 4.

Table 3 presents the results of an experiment of binary acetaldehyde-propylene oxide VLE. Data was obtained for three pressures, 14.7 psia, 29.2 psia, and 60 psia. This binary VLE data set shows a declining acetaldehyde to PO volatility at increasing pressure or temperature. Since the mixtures do not contain methanol, the effect on volatility could be only pressure or temperature although there is a possibility of acetaldehyde dimer or trimer formation. However, the acetaldehyde dimer or trimer formation equilibrium would be similar to hemiacetal/acetal equilibriums; they would be favored at low pressure/temperature. Therefore, the effect of pressure/temperature observed here could be slightly reduced. This set of data was obtained at starting acetaldehyde concentration of 5300 ppm.

TABLE 3

Relative Volatility of Acetaldehyde in Crude Propylene Oxide without methanol[1]

| Pressure (psia) | Temperature (° C.) | Component | Composition (weight percent) Vapor[2] | Composition (weight percent) Liquid[2] | K values | α (AA/PO) |
|---|---|---|---|---|---|---|
| 14.7 | 32 | AA | 0.752 | 0.421 | 1.786 | 1.791 |
|  |  | PO | 99.248 | 99.579 | 0.997 |  |
| 29.2 | 55.7 | AA | 0.717 | 0.461 | 1.556 | 1.560 |
|  |  | PO | 99.283 | 99.529 | 0.994 |  |
| 60.0 | 79.8 | AA | 0.649 | 0.418 | 1.554 | 1.557 |
|  |  | PO | 99.351 | 99.582 | 0.998 |  |

Note:
[1]Contains 0.53% Acetaldehyde
[2]Normalized

Unexpected and beneficial results can also be obtained by reducing the amount of water, methanol, and/or glycol concentration in the solvent-light column 1. With reduced methanol (MeOH) in the crude PO stream 10, both formaldehyde and acetaldehyde removal can be improved, as indicated by the reduced aldehyde level in overhead product stream 34 from the solvent stripper column 3. VLE (Table 4) showed that acetaldehyde relative volatility to PO declines with increased methanol concentration.

Table 4 presents VLE data for PO-acetaldehyde-methanol system, for the effect of methanol on acetaldehyde volatility in propylene oxide. The results demonstrate that at atmospheric pressure or low temperature, acetaldehyde volatility to PO declines with increasing methanol concentration in PO. As methanol concentration reaches about 2.5-3 wt %, acetaldehyde volatility to PO is approaching 1 which makes acetaldehyde inseparable from PO. When methanol concentration increases to about 4 wt %, acetaldehyde become heavier than PO with a relative volatility to PO near 0.82. This phenomenon is believed to be caused by the formation of hemiacetal and acetal at increased methanol concentration even though acetaldehyde concentration was low at only around 50 ppm. Additional VLE data were obtained at about 3 wt % methanol and elevated pressure or increased temperature. By comparing data obtained at atmospheric pressure, 16 psig and 28.7 psig, the results show that acetaldehyde volatility to PO increases with increasing pressure or temperature when methanol is present at a same methanol concentration. The equilibrium formation of hemiacetal/acetal becomes less favored at elevated temperatures. Thus, it is desirable to remove methanol first so that aldehydes will distill overhead in the solvent-lights column 1. If aldehydes are not completely removed, it is desirable to increase the pressure of the solvent-lights column 1 to break the hemiacetals, so that the aldehydes can be taken overhead.

TABLE 4

VLE of Synthetic PO-AA-MeOH Mixtures at Atmospheric Pressure

| Run # | T (° C.) | P (mmHg) | Component | Composition (by weight) Vapor | Composition (by weight) Liquid | K values | α (AA/PO) |
|---|---|---|---|---|---|---|---|
| 1 | 33.3 | 755.8 | AA | 96 ppm | 56 ppm | 1.74 | 1.74 |
|  |  |  | MeOH | — | 5 ppm | — |  |
|  |  |  | PO | 99.9904% | 99.9939% | 1.00 |  |
| 2 | 33.0 | 754.3 | AA | 99 ppm | 57 ppm | 1.79 | 1.76 |
|  |  |  | MeOH | 582 ppm | 666 ppm | 0.87 |  |
|  |  |  | PO | 99.93199% | 99.9278% | 1.00 |  |
| 3 | 33.4 | 748.4 | AA | 85 ppm | 53 ppm | 1.61 | 1.61 |
|  |  |  | MeOH | 0.3772% | 0.4984% | 0.76 |  |
|  |  |  | PO | 99.6143% | 99.4963% | 1.00 |  |
| 4 | 32.8 | 747.5 | AA | 83 ppm | 51 ppm | 1.62 | 1.62 |
|  |  |  | MeOH | 0.8165% | 1.0476% | 0.78 |  |
|  |  |  | PO | 99.1752% | 98.9493% | 1.00 |  |
| 5 | 32.4 | 754.3 | AA | 68 ppm | 51 ppm | 1.35 | 1.33 |
|  |  |  | MeOH | 2.3812% | 3.4437% | 0.69 |  |
|  |  |  | PO | 97.612% | 96.5512% | 1.01 |  |
| 6* | 34.7 | 750.9 | AA | 56 ppm | 52 ppm | 1.09 | 1.08 |
|  |  |  | MeOH | 2.6061% | 3.50% | 0.74 |  |
|  |  |  | PO | 97.3883% | 96.4856% | 1.01 |  |
| 7 | 32.7 | 755.1 | AA | 44 ppm | 52 ppm | 0.86 | 0.84 |
|  |  |  | MeOH | 3.7000% | 5.8658% | 0.63 |  |
|  |  |  | PO | 96.2956% | 94.1290% | 1.02 |  |
| 8 | 33.5 | 746.9 | AA | 44 ppm | 52 ppm | 0.85 | 0.82 |
|  |  |  | MeOH | 4.2013% | 7.1129% | 0.59 |  |
|  |  |  | PO | 95.7943% | 92.8819% | 1.03 |  |
| 9* | 34.7 | 750.9 | AA | 56 ppm | 52 ppm | 1.09 | 1.08 |
|  |  |  | MeOH | 2.6061% | 3.5092% | 0.74 |  |
|  |  |  | PO | 97.3883% | 96.4856% | 1.01 |  |
| 10* | 56.4 | 16 psig | AA | 63 ppm | 48 ppm | 1.33 | 1.32 |
|  |  |  | MeOH | 2.9799% | 3.3628% | 0.89 |  |
|  |  |  | PO | 97.0138% | 96.6325% | 1.00 |  |

TABLE 4-continued

VLE of Synthetic PO-AA-MeOH Mixtures at Atmospheric Pressure

| Run # | T (° C.) | P (mmHg) | Component | Composition (by weight) | | K values | α (AA/PO) |
|---|---|---|---|---|---|---|---|
| | | | | Vapor | Liquid | | |
| 11* | 68.1 | 28.7 psig | AA | 67 ppm | 47 ppm | 1.42 | 1.42 |
| | | | MeOH | 3.2594% | 3.3560% | 0.97 | |
| | | | PO | 96.7339% | 96.6393% | 1.00 | |

*Run # 6 was conducted in a steel recirculation still.
*Runs # 9-11 were conducted in a stainless-steel still.

The water wash apparatus 2 will is now described in greater detail. The wash inlet stream 13 from the solvent-lights column 1 can be sent to water wash apparatus 2. The water wash in water wash apparatus 2 can be carried out by mixing the wash inlet stream 13 (having propylene oxide and impurities) with water and solvent. In particular, water supplied via water inlet stream 20 can be used to remove the impurities from propylene oxide. A solvent (from stream 33) can be used to reduce propylene oxide loss into the water phase. Adequate mixing is beneficial to accomplish preferable impurity removal. Adequate coalescing, and enough residence time in the water wash apparatus 2 is also beneficial to reduce entrainment of the aqueous phase in the organic effluent. The organic effluent can be recycled back to the solvent-lights column 1 via recycle stream 21. An aqueous purge stream 22 with a high concentration of impurities can be purged from the water wash apparatus 2.

The organic effluent in recycle stream 21 can include an amount of aqueous phase within a range having a lower limit and/or an upper limit, each expressed as weight percentages. The range can include or exclude the lower limit and/or the upper limit. The lower limit and/or upper limit for the amount of the aqueous phase in the organic effluent of the wash can be selected from 0, 0.01, 0.02, 0.03, 0.04, 0.05, 0.1, 0.2, 0.3, 0.4, 0.5, 0.7, 1, 2, 3, 4, 5, 6, 7, 8, 9, and 10, weight percent. For example, less than 0.1% of the aqueous phase can be present in the organic effluent of the wash or 10% of the aqueous phase can be present in the organic effluent of the wash.

Key light impurities to remove are methyl formate, formaldehyde, acetaldehyde, and methanol. Most of these impurities in the solvent-lights column overhead stream 11 (an example of an impurity stream) can be removed through a combination of remaining vapor stream 12 and aqueous purge stream 22 from water wash apparatus 2. Lab water wash tests have demonstrated the effective removal of these key light impurities.

The solvent stripper column 3 is now described in greater detail. The solvent stripper column 3 can be made of any suitable material, including but not limited to stainless steel or carbon steel. The solvent stripper column 3 can include any suitable number of trays or theoretical trays, for example, about 10 trays. Solvent-lights reboiler bottoms stream 17 can be added at tray 1-10, for example at tray 5. A packing material can be employed in the solvent stripper column 3 to enhance vapor-liquid contact. Suitable packing materials can be made from any material including glass, metal, plastic, and ceramic. If packing is used, it can be structured or dumped, and the like. If trays are used, then can be sieve trays, bubble cap trays or valve trays, and so on.

Figure 2:
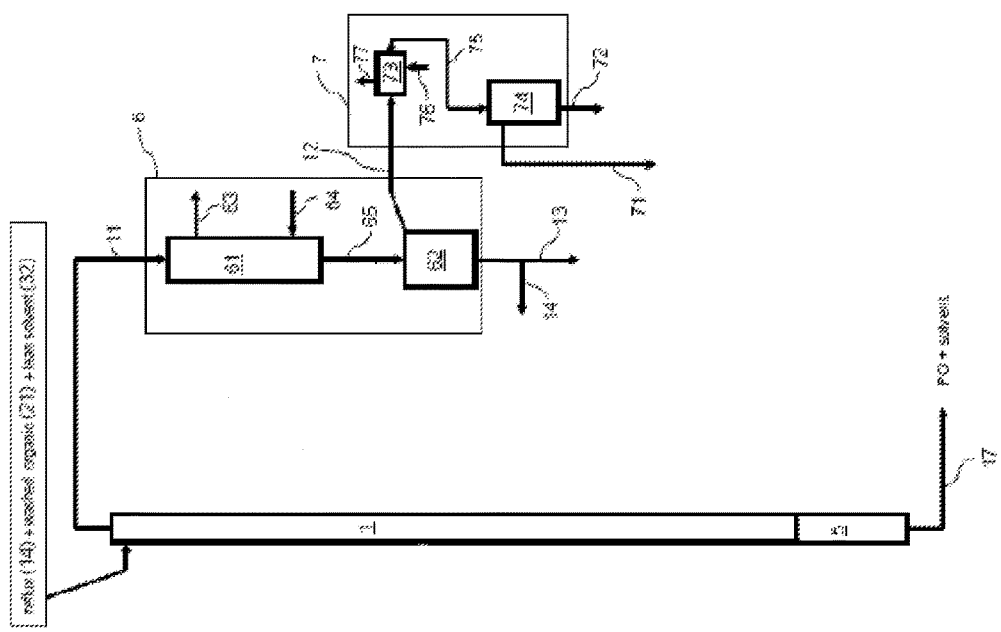
FIG. 2 is a schematic, including a solvent-lights column, according to one embodiment, as used in a pilot plant.

Referring to FIG. 2, more exemplary detail of the solvent-lights column 1, the cooler system 6, and overhead condenser system 7 is shown. In operation, the overhead stream 11 from the solvent-light column 1 can be passed into a cooler 61, which utilizes cooling fluid introduced via cooling inlet line 64 and removed via cooling outlet line 63. The partially condensed outlet stream 65 from the cooler 61 flows into a reflux drum 62. Liquid from the reflux drum 62 may be split into the reflux stream 14 and the wash inlet stream 13 mentioned above with respect to FIG. 1. The remaining vapor stream 12 from the reflux drum 62 can be fed to a vapor condenser 73, supplied with cooling glycol (or other refrigerant or cooling medium) which enters the vapor condenser 73 via refrigerant inlet 76 and exits via refrigerant outlet 77. The condenser outlet 75 can be fed into a separator 74 to give the vapor purge stream 71 and the liquid purge stream 72 mentioned above with respect to FIG. 1.

Figure 3:
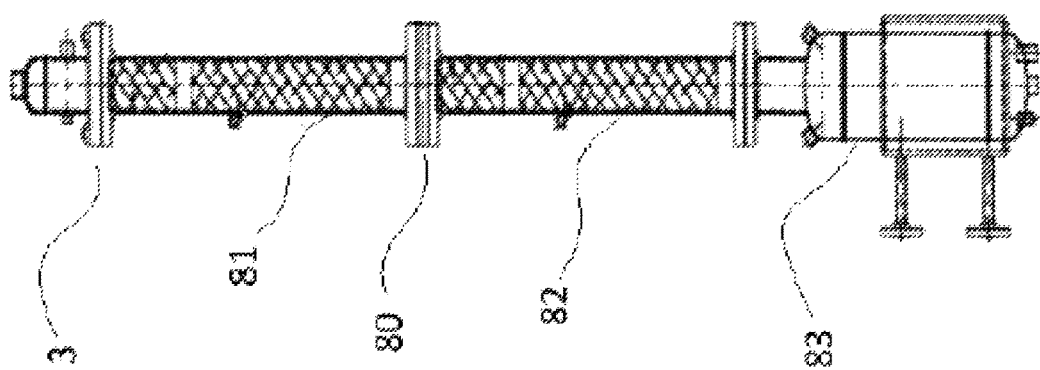
FIG. 3 is a schematic of a solvent stripper column, according to one embodiment, as used in a pilot plant.

Referring to FIG. 3, the solvent stripper column 3, according to one embodiment as used in a pilot plant, is depicted in greater detail. Note that the specific dimensions referenced below refer to one particular embodiment and are not meant to limit the scope of the claimed invention. The solvent stripper column 3 was made from 3" Schedule 40 pipe. The entire height including the solvent stripper column reboiler 83 was 88 inches tall. The solvent stripper column 3 included a first packed section 81 and a second packed section 82, each packed section was 28¾ inches tall with 24 inches of packing. The packing was made of 0.24" Pro-pak™ packing, supported by conical screens resting on rings welded to the internal diameter of the column. Distribution rings were also used at the top of each packed section to ensure even distribution of liquid from above, over the packing.

Still referring to FIG. 3, the feed point 80 was in the middle of the vertical height of solvent stripper column 3, between the first packed section 81 and the second packed section 82. A feed, depicted as solvent-lights reboiler bottoms stream 17 in FIG. 1, was added to the solvent stripper column 3 at the feed point 80. The solvent stripper column 3 was operated at 4 to 5 psig. The steam flow to the solvent stripper column reboiler 83 at the base of the stripper column 3 was controlled to hold the weight percentage of PO in the bottoms at 0.5 to 1.5 wt %. Vapor was removed from the top of the stripper column 3, and fed to a total condenser (not shown in FIG. 3). The condensed liquid was split into two parts. One part was fed back to the top of the solvent stripper column 3 as reflux. The rest of the liquid distillate was taken as the overhead product stream 34 shown on FIG. 1.

EXAMPLES

The following examples were carried out in a continuous pilot plant. The overview of the pilot unit is shown in FIG. 1. Additional details of a solvent-lights column 1, used in the examples are shown in FIG. 2. Additional details of solvent stripper column 3 are shown in FIG. 3. The solvent-lights column 1 employed in the examples had a 2" inside diameter and contained a bed of Pro-pak™ stainless steel protruded packing that was 11 feet deep. The Pro-pak™ stainless steel protruded packing was 0.24" size. The solvent stripper column 3 in FIG. 1 is also shown in more detail on FIG. 3. The solvent stripper column 3 was 3" inside diameter and contained a bed of Pro-pak™ stainless steel protruded packing, 0.24" size, which was 4 feet deep.

Example 1

Example 1 describes the test period when the pilot unit solvent-lights column 1 as shown in FIGS. 1 and 2 was operated first at 25 psig. The crude PO stream 10 comprising crude propylene oxide (an intermediate stream from a PO/TBA process) was fed to a point on the solvent-lights column 1 at the middle of the column. Table 5 shows the concentrations of key impurities in the feed stream, each expressed as a weight percentage of the total composition.

TABLE 5

| Component | Average weight percent |
| --- | --- |
| MeF | 0.06 |
| Methanol | 0.1172 |
| Acetaldehyde | 0.03 |
| Water | 0.16 |
| Formaldehyde | 0.005 |

A plurality of temperature probes extending into the solvents lights column 1 were positioned along the vertical length of the solvent-lights column 1.

The temperature of the crude PO stream 10 was 27 degrees Celsius and the flow rate was 3.0 kg/hr. Stream 32, having a lean solvent, pumped from the bottom of the solvent stripper column 3, was introduced at the top of the solvent-lights column 1 as shown in FIG. 1. (The solvent stripper column 3 is also shown in greater detail in FIG. 3.) The flow rate of lean solvent in stream 32 was 21.5 kg/hr. Reflux stream 14 was introduced into solvent-lights column 1 at a rate of 1.5 kg/hr.

Wash inlet stream 13 was introduced into water wash apparatus 2 at a rate of 185 gm/hr. Two other streams were fed to the water wash apparatus 2: deionized water at a rate of 100 gm/hr and lean solvent from the bottom of the solvent stripper at a rate of 2.4 kg/hr. The water wash apparatus 2 consisted of three parts: a mixer, a coalescer and a decanter. The mixer was a 4-inch section of ⅟₁₆" OD tubing having an inside diameter of 0.030". Downstream of the mixer was a coalescer (not illustrated) which was a 1-foot long bed of glass wool in a ⅜" OD tube. Downstream of the coalescer was a decanter (not illustrated) where the organic and aqueous phases were separated. The decanter was a vertical glass pipe, 2.0" ID by 12" tall. The washed organic phase overflowed from the top of the decanter and was sent to the top of the solvent-lights column 1. The aqueous bottom layer from the decanter, rich in methanol, methyl formate, acetaldehyde and formaldehyde, was sampled and collected. The organic and aqueous products from the decanter were used to calculate partition coefficients for the key impurities, as shown in Table 6. Partition Coefficient for each component (i) was calculated based on the following definition:

$$\text{Partition Coefficient} = \frac{\text{Weight fraction in Aqueous phase}}{\text{Weight fraction in Organic phase}}$$

TABLE 6

| Component | Average Partition Coefficient |
| --- | --- |
| Methyl Formate | 1.6 |
| Methanol | 57 |
| Acetaldehyde | 6.6 |
| PO | 0.8 |
| Formaldehyde | 190 |

Table 6 shows that methanol, acetaldehyde and formaldehyde are easily extracted by the water wash block, since the partition coefficients are high.

Table 7 provides exemplary temperature, pressure and flow rate data for the pilot unit operation.

TABLE 7

| Stream | Temperature | Pressure | Flow Rate |
| --- | --- | --- | --- |
| 10 | 69-84° C. | 25-30 psig | 2.7-3.3 kg/hr |
| 11 | 77-84° C. | 25-30 psig | 1.65-1.72 kg/hr |
| 12 | 63-72° C. | 25-30 psig | 2-13 gm/hr |
| 13 | 50-68° C. | 25-30 psig | 160-200 gm/hr |
| 14 | 50-68° C. | 25-30 psig | 1.49-1.5 kg/hr |
| 15 | 106-119° C. | 25-30 psig | 24-28 kg/hr |
| 16 | 106-119° C. | 25-30 psig | |
| 17 | 16-20° C. | 25-30 psig | 24-28 kg/hr |
| 20 | 20-26° C. | 25-30 psig | 100-101 gm/hr |
| 21 | 43-46° C. | 25-30 psig | 2.3-2.8 kg/hr |
| 22 | 43-46° C. | 25-30 psig | 102-118 gm/hr |
| 31 | 20-26° C. | 25-30 psig | 22.2-25.6 kg/hr |
| 32 | 20-26° C. | 25-30 psig | 20-23 kg/hr |
| 33 | 20-26° C. | 25-30 psig | 2.2-2.6 kg/hr |
| 34 | 69-84° C. | 3-4 psig | 2.7-3.3 kg/hr |

The vapors from solvent-lights column 1, which did not condense in cooler 61 shown in FIG. 2 were collected and analyzed. The solvent-lights reboiler bottoms stream 17 from the solvent-lights column 1 was sent to the middle of the solvent stripper column 3, as shown FIG. 1. The solvent stripper column 3 was operated at 4 psig. A purpose of the solvent stripper column 3 was to recover the propylene oxide product as a distillate (overhead product stream 34) and the lean solvent as the bottoms product stream 31. The feed rate to the solvent stripper column 3 was 26.9 kg/hr. The reflux rate to the solvent stripper column 3 was 8.0 kg/hr. As mentioned earlier, the bottoms product stream 31 from the solvent stripper column 3 was split into two streams (via stream 32 and stream 33), with stream 32 feeding the top of the solvent-lights column 1 and stream 33 feeding the water wash apparatus 2 on FIG. 1.

As the pressure of the solvent-lights column 1 was increased from 25 psig to 30 psig, the operating temperatures at the solvent-light column 1 also increased by about 5 degrees Celsius. At higher column temperature, a large amount of hemiacetals and/or acetals are converted to the form of aldehyde plus alcohol. Aldehyde and alcohol are then distilled overhead in the solvent-lights column 1 and removed by both water wash and vapor purge.

Formaldehyde is primarily removed into aqueous purge. Acetaldehyde is removed into both purges. As shown in Table 6 water wash operation, formaldehyde is favorably partitioning into the aqueous phase.

As shown in Table 8, with higher temperatures at the solvent-lights column 1, formaldehyde in the final pilot plant product (contained in overhead product stream 34 from the solvent stripper column 3) is reduced from 25.4 ppm to 7.8 ppm and acetaldehyde is reduced from 6.4 ppm to 4.8 ppm. This was an unexpected and extremely beneficial result.

TABLE 8

Impact of Higher Distillation Pressure and Temperature on Aldehyde Removal

| | Solvent-Lights Column 1 | | Solvent-Lights Column 1 Overhead (wash inlet stream 13) | | Solvent Stripper Overhead Product Stream 34 | |
|---|---|---|---|---|---|---|
| Pressure (psig) | Solvent-Light Overhead 11 Temp (° C.) | Solvent-light bottom product 15 Temp (° C.) | Avg. Formaldehyde, (wt. %) | Avg. Acetaldehyde, (wt. %) | Average Formaldehyde (ppm) | Average Acetaldehyde (ppm) |
| 25 | 77.1 | 78.5 | 0.0422 | 1.222 | 25.4 | 6.4 |
| 30 | 82.1 | 83.1 | 0.0683 | 1.266 | 7.8 | 4.8 |

Example 2

Unexpectedly beneficial results can also be obtained by reducing the amount of water, methanol, and/or glycol concentration in the solvent-lights column 1 feed. Two methanol (MeOH) concentrations were tested using the same pilot unit as describe in Example 1. One test used a propylene oxide feed containing 0.1172 wt % MeOH, as shown in Table 5. The other test used a feed having 0.0032 wt % of MeOH, as shown in Table 9. The feed stream comprising a propylene oxide feed stream was a crude PO stream from a PO/TBA process. Both Table 5 and Table 9 show the concentrations of key impurities in the feed stream, each expressed as a weight percentage of the total composition of a crude PO stream from a PO/TBA process.

TABLE 9

| Component | Average weight percent |
|---|---|
| MeF | 0.06 |
| Methanol | 0.0032 |
| Acetaldehyde | 0.03 |
| Water | 0.16 |
| Formaldehyde | 0.005 |

With reduced MeOH in PO feed, both formaldehyde and acetaldehyde removal was unexpectedly improved, as indicated by the reduced aldehyde level in solvent stripper overhead product stream 34. Without wishing to be bound by theory, it is possible that the improvement is due to both enhanced aldehyde-propylene oxide vapor liquid equilibrium (VLE) and less carryover of hemiacetals or acetals into the solvent stripper column 3 from the solvent-light column 1. Table 10 summarizes the results obtained.

TABLE 10

Impact of Methanol Concentration on Aldehyde Removal

| | Crude PO Feed 10 | | | |
|---|---|---|---|---|
| | Solvent Light Column Overhead (wash inlet stream 13) | | Overhead Product Stream 34 | |
| wt % MeOH | Average Formaldehyde (wt %) | Average Acetaldehyde (wt %) | Average Formaldehyde (ppm) | Average Acetaldehyde (ppm) |
| 0.1172 | 0.0683 | 1.266 | 7.8 | 4.8 |
| 0.0032 | 0.0736 | 1.275 | 3.6 | 3.5 |

Figure 4:
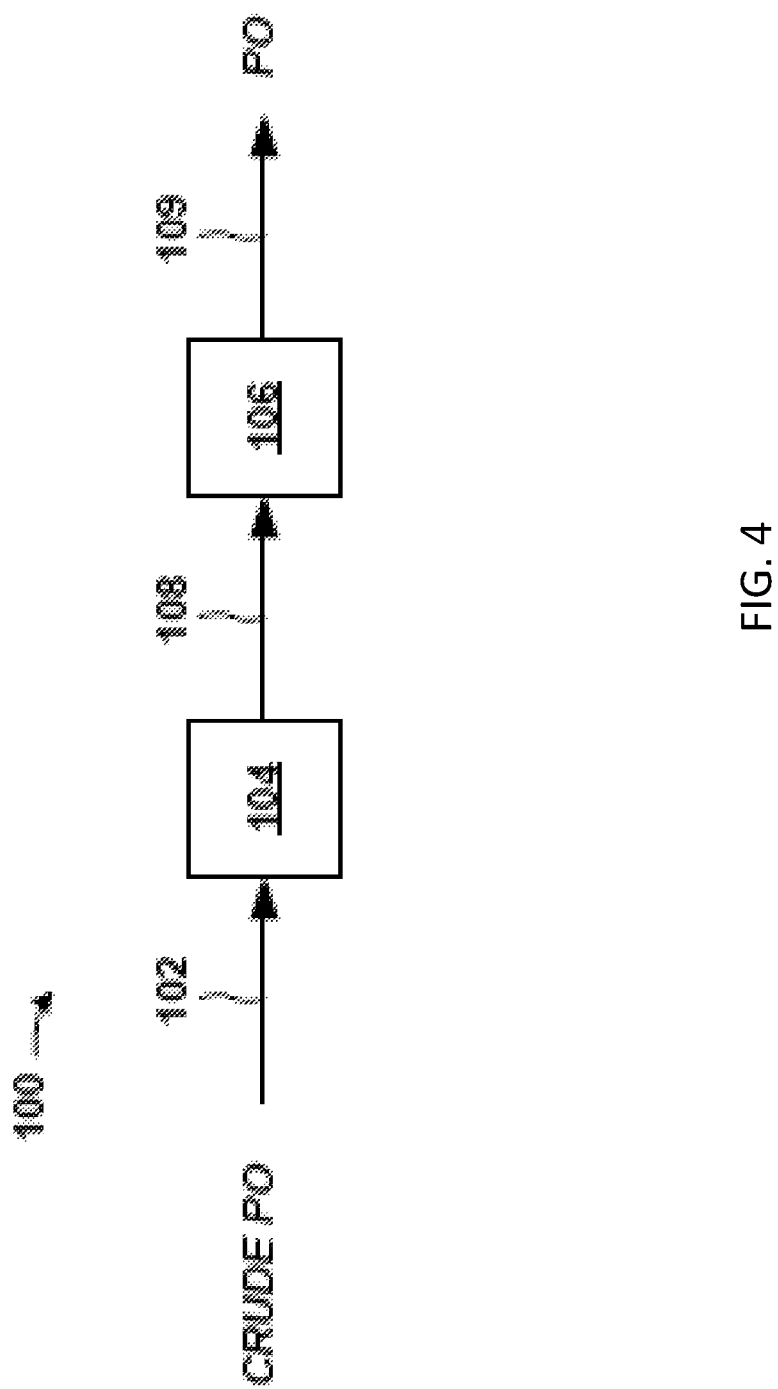
FIG. 4 is a schematic block diagram of a propylene oxide separation system according to various embodiments.

FIG. 4 is an overview of an exemplary propylene oxide (PO) separation system 100 for removing impurities from a crude propylene oxide (PO) stream 102 from a PO/TBA reactor process. The crude PO stream 102 may be an effluent stream from a reactor of a PO/TBA process, for example, and may include impurities described above along with the desired product, PO.

In certain examples, the crude PO stream 102 is not subjected to upstream removal of heavy components such as in a heavies column prior to being fed to the PO separation system 100. Thus, the crude PO stream 102 entering the PO separation system 100 may have a significant amount of water and methanol, for instance. Examples of impurities given in exemplary weight percentage of the crude PO stream 102 are listed in Table 11. Of course, other weight percentages for these impurities are accommodated by the present techniques.

TABLE 11

| Component | Average weight percent |
|---|---|
| MeF | 0.06 |
| Methanol | 0.34 |
| Acetaldehyde | 0.03 |
| Water | 0.47 |
| Formaldehyde | 0.0047 |

In embodiments, the PO separation system 100 includes a front-end 104 and a back-end 106. In general, the front-end 104 removes light impurities, water, and water-soluble impurities (e.g., methanol) from the crude PO stream 102, as well as some solvent, and discharges a PO stream 108 having PO, hydrocarbon solvent, and some impurities to the back-end 106. In certain embodiments, the level of impurities in the PO stream 108 is relatively low and predominant components may be PO and solvent. The back-end 106 generally removes the hydrocarbon solvent (and impurities) from the PO stream 108 to give PO product stream 109.

Hydrocarbon solvent may be added (not shown) to the front-end 104 to facilitate formation of aqueous (water) and organic (solvent) phases in the front-end 104. The PO typically has an affinity for the organic (solvent) phases/streams in the front-end 104. Again, the back-end 106 removes the hydrocarbon solvent from the PO stream 108 and discharges a PO product stream 109. The source of the hydrocarbon solvent to the front-end 104 may be solvent recycled from the back-end 106 and/or fresh solvent.

As discussed in detail below, the front-end 104 of the separation system 100 may include a distillation column, such as a solvent-lights column, and a solvent stripper column, and the like. Again, the front-end 104 removes light impurities and aqueous impurities from the crude PO stream 102, and forwards a PO stream 108 to the back-end 106. The PO stream 108 may be further processed in a back-end 106 of the separation system 100 which may include an extraction column, solvent column, and PO product column, and so forth. The back-end 106 subjects the crude PO to solvent extraction and also removes light and heavy impurities to give PO product stream 109.

As also discussed below, to facilitate removal in the front-end 104 of at least the water and methanol impurities from the crude PO stream 102 and from the solvent-lights column, the techniques may beneficially provide for a combination (FIG. 5) of a decanter and water wash on the solvent stripper column overhead, and/or a side draw (FIG. 7) from the solvent-lights column. Moreover, in general, the present techniques may advantageously provide for a grassroots facility or for retrofit of existing equipment and operations.

Figure 5:
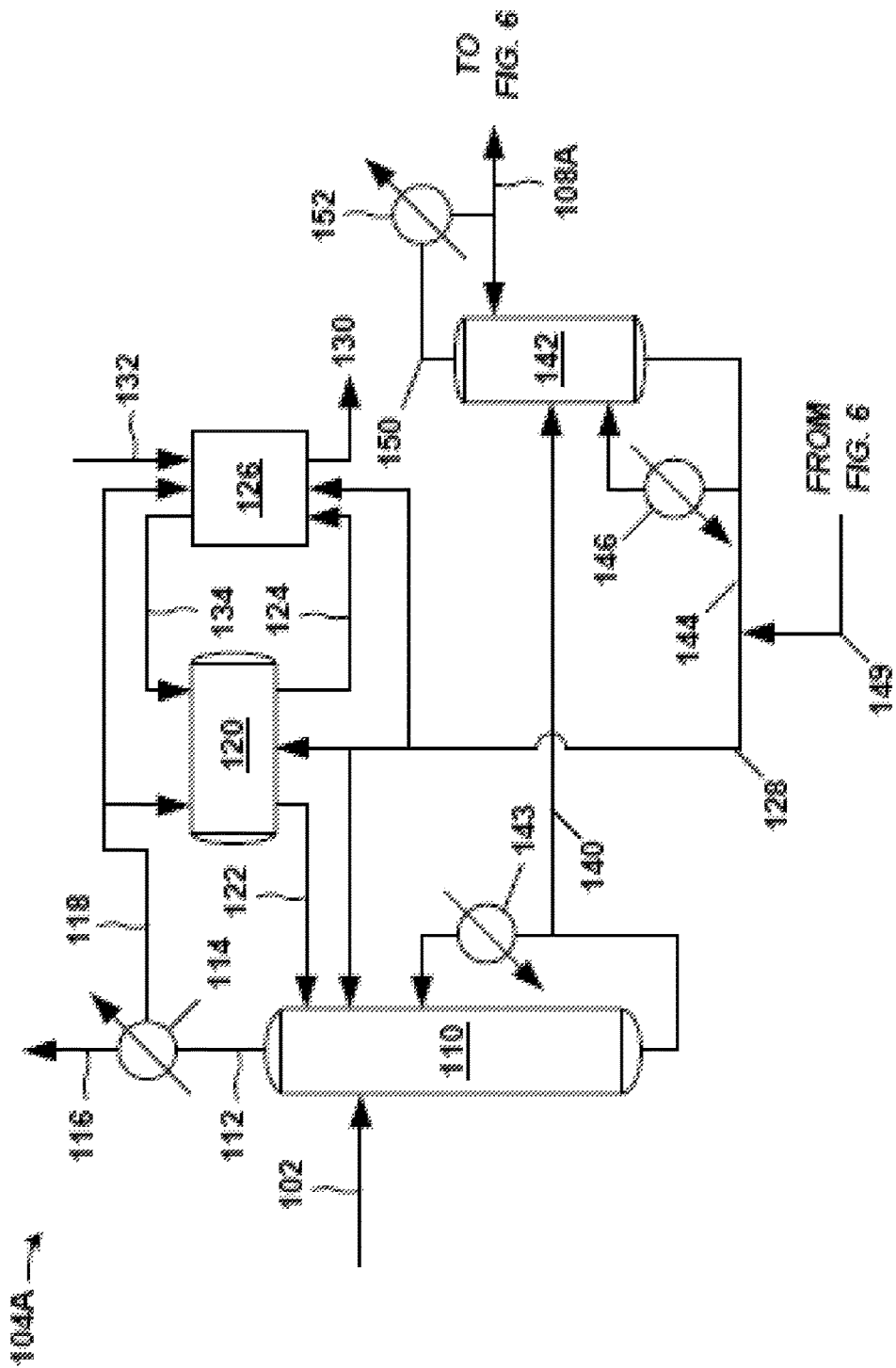
FIG. 5 is a schematic block diagram of a front-end of a propylene oxide separation system according to one embodiment.

FIG. 5 is an exemplary front-end 104A of the propylene oxide separation system 100. The crude PO stream 102 (e.g., a PO reactor effluent stream of a PO/TBA process) is fed into a distillation column, such as solvent-lights column 110. A majority of the PO and hydrocarbon solvent in the incoming crude PO stream 102 discharges in a product stream (bottoms stream 140) from the bottom of the solvent-lights column 110. (As noted below, bottoms stream 140 is the portion of the bottoms discharge from the solvent-lights column 110 not recycled to the solvent-lights column 110 through the solvent-lights reboiler 143.) Most of the impurities such as light and aqueous impurities in the crude PO stream 102 are removed in an overhead stream 112 and sent to an overhead condenser 114 (e.g., shell and tube heat exchanger). The overhead condenser 114 may provide for partial condensation of the overhead stream 112 in certain examples. A cooling medium (e.g., cooling tower water) is fed to the utility side of the overhead condenser 114 in embodiments.

Components in the overhead stream 112 entering the overhead condenser 114 that are not condensed can be purged from the system 100 (or front-end 104A) via a vapor stream 116 purge. These non-condensed components in vapor stream 116 may be sent to another process, discharged as waste, and the like. If desired, the non-condensed components in vapor stream 116 may be subjected to further local processing, such as in an additional condenser operating at lower temperature than the overhead condenser 114, and so forth. The non-condensed components in vapor stream 116 may include acetaldehyde, methyl formate, and other undesired impurities.

A condensed overhead stream 118 discharges from the process side of the overhead condenser 114 and is sent to a decanter 120, which provides residence time for separation of an organic phase and an aqueous phase (not shown in the figures). In one example, the amount of water and methanol in condensed overhead stream 118 is 4 weight % water and 3 weight % methanol. An organic stream 122 from the organic phase in decanter 120 may be sent as reflux to the solvent-lights column 110. An aqueous stream 124 from the aqueous phase in decanter 120, which has the majority of the methanol and water in the portion of the condensed overhead stream 118 entering decanter 120, may be sent from decanter 120 to a water wash system 126 in this example.

Thus, the decanter 120 may facilitate removal of relatively large amounts of water and methanol from the condensed overhead stream 118 so that beneficially less water and less methanol are refluxed back to the solvent-lights column 110. Therefore, advantageously, lower amounts of methanol and water accumulate in the solvent-lights column 110. Use of the organic stream 122 as the relatively dry reflux reduces the probability of separate water phase formation in the solvent-lights column 110.

Solvent 128 (discussed below), which may be a hydrocarbon (e.g. C8-C10), may be added to the solvent-lights column 110, to the decanter 120, and/or to the water wash system 126. Addition of solvent 128 to the decanter 120 may facilitate the formation and separation in the decanter 120 of the aqueous phase having the undesired methanol and water. As indicated, an aqueous stream 124 is sent from the decanter 120 to the water wash system 126 to discharge impurities such as methanol, water, methyl formate, acetaldehyde, glycols, and the like, from the system 100 (or front-end 104A) via the downstream aqueous purge 130 of the water wash system 126.

Water 132 (e.g., tap water, treated water, demineralized water, etc.) is added to the water wash system 126 to drive the downstream aqueous purge 130 of impurities from the system 100. The water wash system 126 may have a vessel or coalescer (not shown), for example, to provide volume for the water wash. The water wash system 126 may also include an upstream mixer, for example a static mixer (also not shown) to provide for mixing of the aqueous stream 124 and the solvent 128 prior to entry to the vessel or coalescer of the wash system 126. Of course, other configurations for the water wash system 126 may be accommodated.

A source of glycol impurities may be various solvents in the system 100 that deteriorate over time in the presence of water and methanol, for instance, to form glycols. An advantage of removing the impurities (for example, water and methanol) is that the hydrocarbon solvents present in the system 100 may deteriorate less.

A wash organic stream 134 is sent from the water wash system 126 to the decanter 120 for eventual reflux to the solvent-lights column 110 (via organic stream 122). Further, optionally, a portion of the condensed overhead stream 118 from the overhead condenser 114 may bypass the decanter 120 and be sent directly to the water wash system 126. In the embodiment of FIG. 5, a portion of the condensed overhead stream 118 is sent to the decanter 120 and a portion bypasses the decanter 120 for the water wash system 126.

The present techniques provide unique embodiments of the overhead configuration of the solvent-lights column 110 to remove light impurities via a vapor purge of non-condensed components (vapor stream 116) and via a downstream aqueous purge 130 from the water wash system 126. The decanter 120 provides volume and residence time, and a unit operational to receive solvent addition to allow formation of the aqueous phase (giving aqueous stream 124) having significant amounts of water, methanol, and other aqueous-phase impurities.

Advantageously, removal of these light impurities such as methyl formate, formaldehyde, acetaldehyde, and methanol via the downstream aqueous purge 130 (and thus reducing the amount of such impurities in the reflux to solvent-lights column 110) reduces hemiacetal or acetal formation in the solvent-lights column 110. Such heavier-formed components have lower boiling points and could undesirably discharge in the product stream (bottoms stream 140) from solvent-lights column 110. Further, these hemiacetal or acetal compounds could later breakdown in downstream columns into aldehydes and contaminate the PO product.

As indicated, present embodiments of the solvent-lights column 110 and its overhead configuration reduce hemiacetal or acetal formation in the solvent-lights column 110. Moreover, the disclosed techniques facilitate capability for the front-end 104A of the separation system 100 (FIG. 4) to receive a crude PO stream having relatively high amounts of water and methanol, for example, directly to the solvent-lights column 110.

The aforementioned product stream from the bottom of the solvent-lights column 110 is labeled as bottoms stream 140 in FIG. 5. This bottoms stream 140, having a majority of the PO entering the column 110, can be sent to a solvent stripper 142. As is typical with distillation columns, some of the bottom discharge from the column 110 may be vaporized in a solvent-lights reboiler 143 and returned as vapor to the solvent-lights column 110. Steam or steam condensate, for example, may be fed to the utility side of the solvent-lights reboiler 143. Bottoms stream 140 is the portion of the bottoms discharge from the solvent-lights column 110 not recycled to the solvent-lights column 110 through the solvent-lights reboiler 143. The bottoms stream 140 is processed in the solvent stripper 142 to remove solvent from the PO product in the bottoms stream 140.

Figure 6:
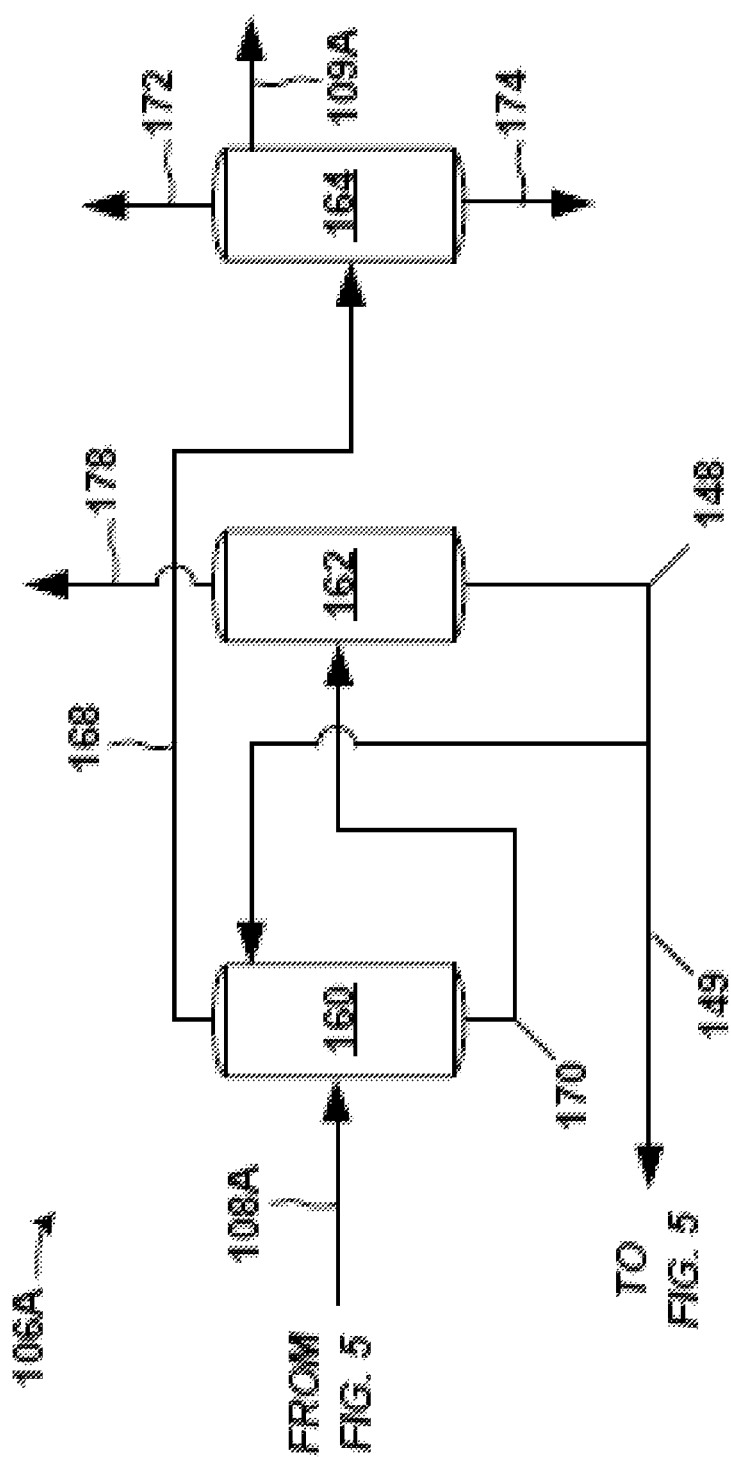
FIG. 6 is a schematic block diagram of a back-end of a propylene oxide separation system associated with the front-end of FIG. 5 according to one embodiment.

At the solvent stripper 142, solvent is removed via a bottoms discharge. A portion of the bottoms discharge may be sent through a solvent stripper reboiler 146 and returned as vapor to the solvent stripper 142. Steam or steam condensate may be fed as the heating medium, for example, to the utility side of the solvent stripper reboiler 146. The remaining bottoms discharge is the solvent stripper bottoms stream 144, which may be combined in this embodiment with fresh solvent or with a solvent recycle such as recycle solvent 149 from the exemplary back end 106A (FIG. 6) of the separation system 100, and so on, to result in the aforementioned solvent 128 fed to the solvent-lights column 110, decanter 120, and/or water wash system 126. The recycle solvent 149 may be from the bottoms stream 148 of a solvent column 162, for example, in the exemplary back-end 106A (FIG. 6).

A majority of the PO received at the solvent stripper 142 via bottoms stream 140 discharges in a solvent stripper overhead stream 150. This solvent stripper overhead stream 150 may be condensed in stripper overhead condenser 152. The cooling medium fed to the utility side of the stripper overhead condenser 152 may be cooling tower water or other cooling fluid. A portion of the condensed solvent stripper overhead stream 150 exiting the condenser 152 may return to the solvent stripper 142 as reflux. The remaining portion of the condensed solvent stripper overhead stream 150 exiting the condenser 152 may be forwarded as a distillate (PO stream 108A in this example) to the exemplary back-end 106A (see FIG. 6) of the separation system 100 (FIG. 4) for further processing to remove impurities from the PO in PO stream 108A. The PO stream 108A sent to the exemplary back-end 106A may be analogous to PO stream 108 of FIG. 4.

Lastly, the exemplary equipment contemplated in the exemplary front end 104A of the separation system 100 may be commercial scale. The respective diameters and heights of the solvent-lights column 110 and the solvent stripper 142 may be sized as a function of the design basis for the mass flow rate and composition of the incoming crude PO stream 102, for instance. Further, in one example, the number of theoretical stages in the solvent-lights column 110 is about 25, and the crude PO stream 102 is fed into the solvents-lights column 110 at about stage 11 to 15. Of course, other total numbers of theoretical stages, and feed points, are contemplated.

To provide for the theoretical stages, trays or packing may be employed, though trays may be typical. Trays may include sieve trays, bubble cap trays or valve trays, and the like. The packing, which may be structured or dumped, can be glass, metal, plastic, and ceramic, and so on. The metallurgy or materials of construction of the various equipment in the exemplary front-end 104A, including the solvent-lights column 110 and the solvent stripper 142, may be carbon steel, stainless steel, fiberglass reinforced polymer (FRP), nickel alloys, and so on. Such metallurgy or materials of construction may also be applicable to the columns and other equipment in the exemplary back-end 106A depicted in FIG. 6.

FIG. 6 is an exemplary back-end 106A associated with the exemplary front-end 104A (FIG. 5) of the separation system 100. The exemplary back-end 106A includes an extraction column 160, solvent column 162, and PO column 164. For the sake of clarity, the respective reboiler and overhead condenser (including any reflux system) for each column 160, 162, and 164 are not shown.

The extraction column 160 receives as feed the portion of the condensed solvent stripper overhead stream 150 from the solvent stripper 142 (FIG. 5) collected as distillate as PO stream 108A. PO stream 108A is subjected to extraction with a solvent (e.g., C8-C10 hydrocarbon) in extraction column 160. The solvent used for extraction may come from the solvent bottoms stream 148 of the downstream solvent column 162. A product stream (extraction overhead stream 168), having the majority of PO entering the extraction column 160, discharges overhead from the extraction column 160. An extraction bottoms stream 170, having solvent and impurities discharges, from the bottom of the extraction column 160.

The extraction overhead stream 168 is condensed and sent to the PO column 164 where an overhead lights purge 172 is removed, a bottoms heavies purge 174 is removed, and a PO product stream 109A is discharged as a product side draw. This PO product stream 109A may be analogous to PO product stream 109 of FIG. 4.

The extraction bottoms stream 170 from the extraction column 160 is fed to the solvent column 162 where a hydrocarbon purge 178 (e.g., C6) is removed overhead and a solvent bottoms stream 148 (e.g., C8-C10) is removed via a bottom discharge. As indicated, all or a portion of this solvent bottoms stream 148 may be fed to the extraction column 160. Also, a take-off portion (recycle solvent 149) of the solvent bottoms stream 148 may be sent to unit operations in the front-end 104A (FIG. 5).

A separation system 100 (FIG. 4) having the front-end 104A (FIG. 5) and back-end 106A (FIG. 6) may give a PO product stream 109A having acceptable levels of impurities (i.e., within typical specifications) and at acceptable PO losses (e.g., less than 2%) in the separation system 100. Exemplary configurations of the front-end 104A give acceptable and relatively low amounts of impurities in the solvent stripper overhead stream 150 (FIG. 5) discharging from the solvent stripper 142. The part per million (ppm) of certain impurities in the solvent stripper overhead stream 150 are given in Table 12 for one example.

TABLE 12

| Component | Ppm |
| --- | --- |
| MeF | <5 |
| Acetaldehyde | ~10 |
| Methanol | 5-10 |
| Water | <50 |

Figure 7:
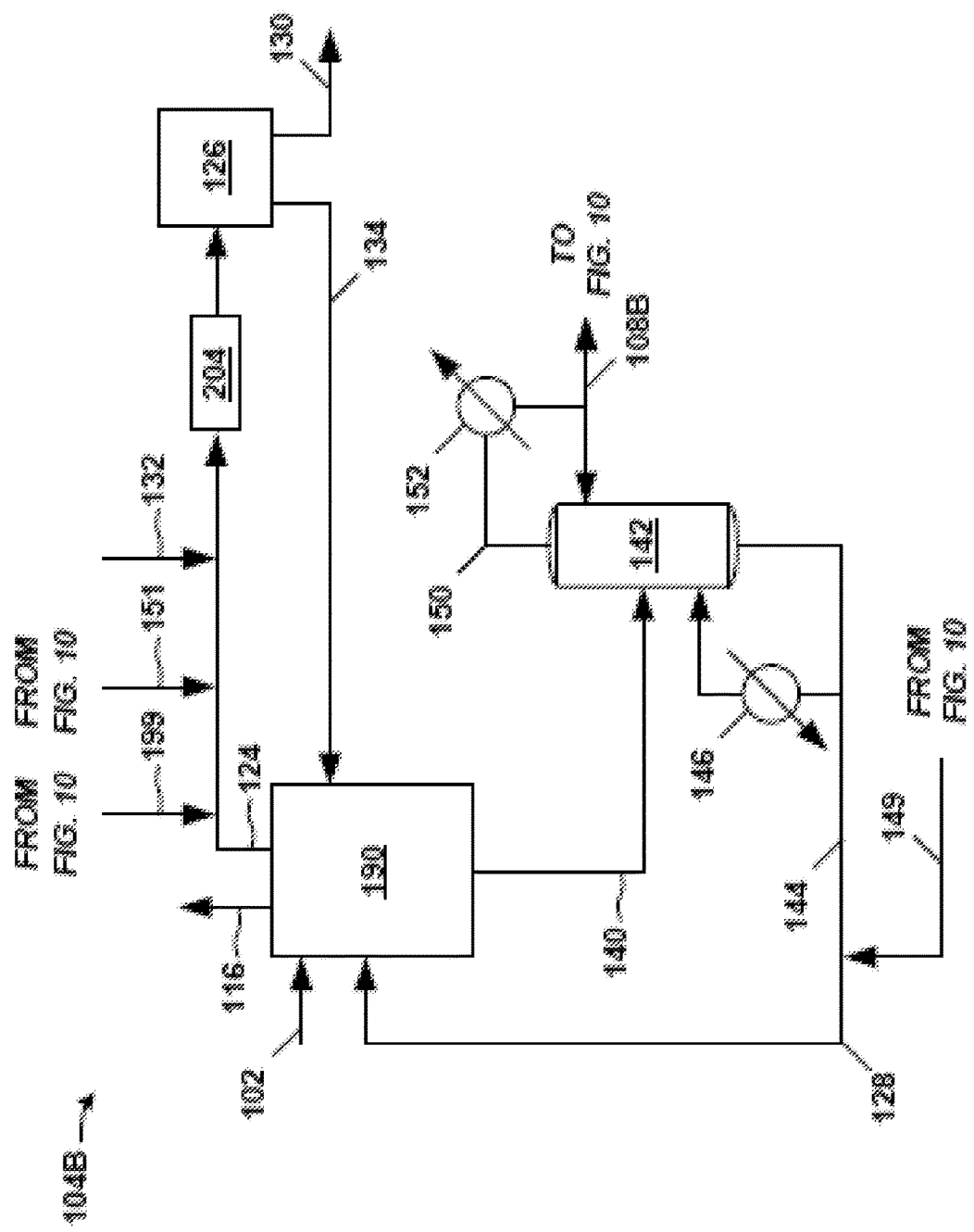
FIG. 7 is a schematic block diagram of another front-end of a propylene oxide separation system according to one embodiment.

FIG. 7 is another example of a front-end 104B of the separation system 100. The crude PO stream 102 is fed to a solvent-lights column system 190. Exemplary details of the solvent-lights column system 190 are given in FIGS. 8 and 9. The solvent-lights column system 190 discharges impurities received from the crude PO stream 102 via a vapor stream 116 purge and an aqueous stream 124. Such impurities may include methanol, water, methyl formate, acetaldehyde, glycols, and the like. The vapor stream 116 purge may be sent to another process or discharged as waste, and so on. The aqueous stream 124 may be from an aqueous phase in a decanter in the solvent-lights column system 190, for example.

The aqueous stream 124 is sent to a water wash system 126. Various solvent-containing streams (e.g., back-end solvent 151 and distillate 199, see below) from the back-end 106B (FIG. 10) and water 132 may be combined with aqueous stream 124 and routed through a mixer 204, for example static mixer, prior to entering the water wash system 126. An example of a solvent stream from the back-end 106B (FIG. 10) added to the aqueous stream 124 may be a back-end solvent 151 from the solvent bottoms stream 148 of a solvent column 162, and so forth. Other streams may be added to the aqueous stream 124 such as overhead distillate 199 from an extraction column 160 to purge formaldehyde from the back-end 106B, for instance.

At the water wash system 126, the aforementioned impurities of methanol, water, methyl formate, acetaldehyde, glycols, and the like, are discharged via a downstream aqueous purge 130. A wash organic stream 134 may be sent from the water wash system 126 to the solvent-lights column system 190. The water wash system 126 may include a vessel or coalescer, and/or other equipment.

The solvent-lights column system 190 discharges a product stream (bottoms stream 140) having a majority of the PO entering the solvent-lights column system 190 in crude PO stream 102. The product stream may be a bottoms stream 140 from a solvent-lights column 110 (a distillation column) in the solvent-lights column system 190 (such as shown in subsequent FIGS. 8 and 9) or the solvent-lights column 110 shown in FIG. 5. The product stream (e.g., bottoms stream 140) is sent to a solvent stripper 142, which may function similarly as discussed above with respect to the front-end 104A (FIG. 5). At the solvent stripper 142, solvent is removed via the solvent stripper bottoms stream 144.

Figure 10:
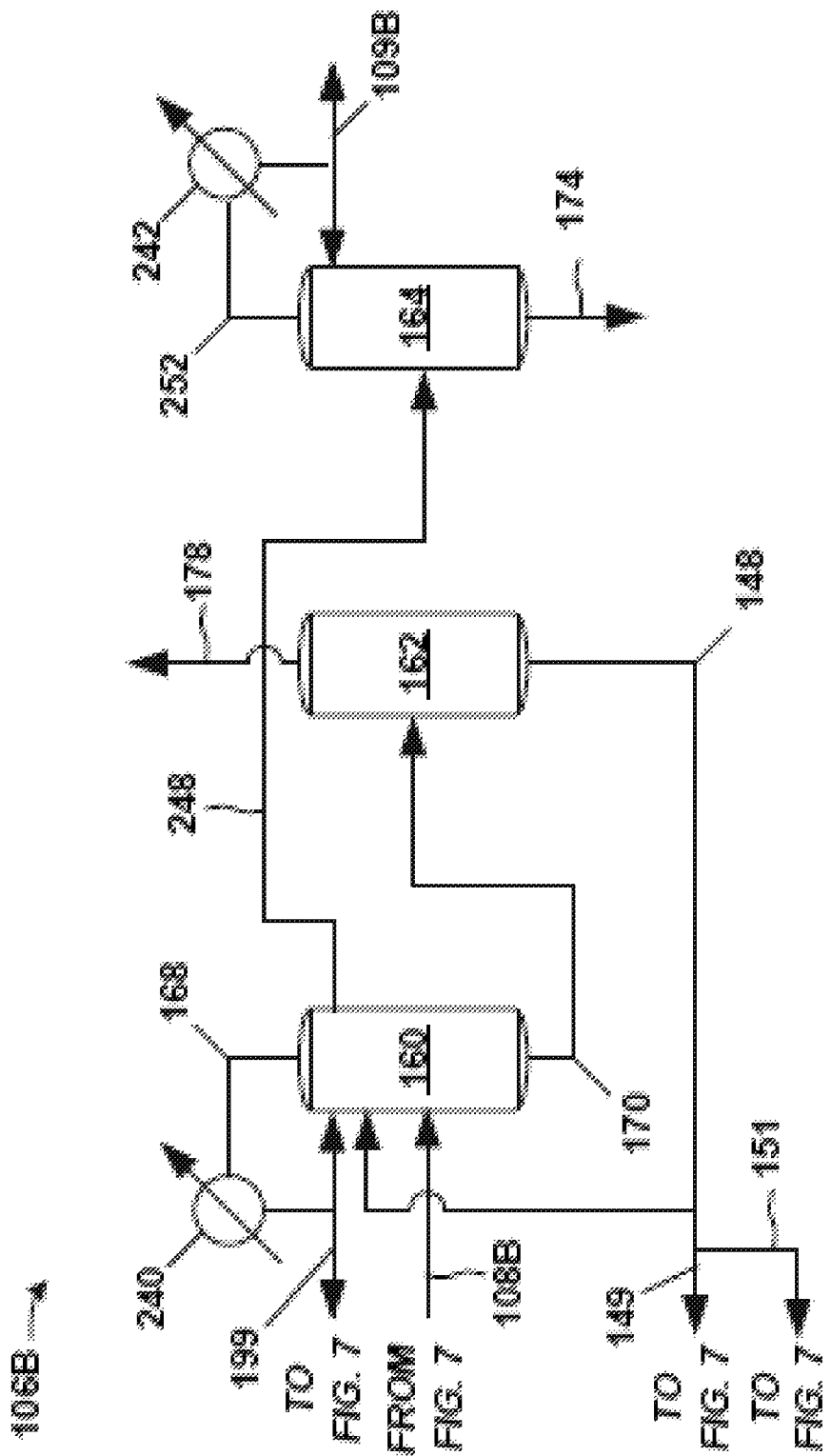
FIG. 10 is a schematic block diagram of a back-end of a propylene oxide separation system associated with the front-end of FIGS. 7-9 according to one embodiment.

The solvent stripper bottoms stream 144 may be sent to the solvent-lights column system 190. Optionally, additional solvent, such as from solvent bottoms stream 148 of the solvent column 162 in the back-end 106B (FIG. 10), may be combined with the solvent stripper bottoms stream 144 to give the solvent 128 in route to the solvent-lights column system 190. Thus, solvent 128 fed to the solvent-lights column system 190 may be the solvent stripper bottoms stream 144 or a combination of the solvent stripper bottoms stream 144 and the recycle solvent 149 from the back-106B (FIG. 10).

A majority of the PO received at the solvent stripper 142 (from bottoms stream 140) discharges in a solvent stripper overhead stream 150. A portion of the condensed overhead stream is forwarded as distillate as PO stream 108B to the back-end 106B (see FIG. 10) of the separation system 100 for further processing to remove impurities from the PO. However, the amount of impurities in the overhead stream 150 and the PO stream 108B is generally relatively low. This stream 108B sent to the back-end 106B may be analogous to the PO stream 108 of FIG. 4.

Figure 8:
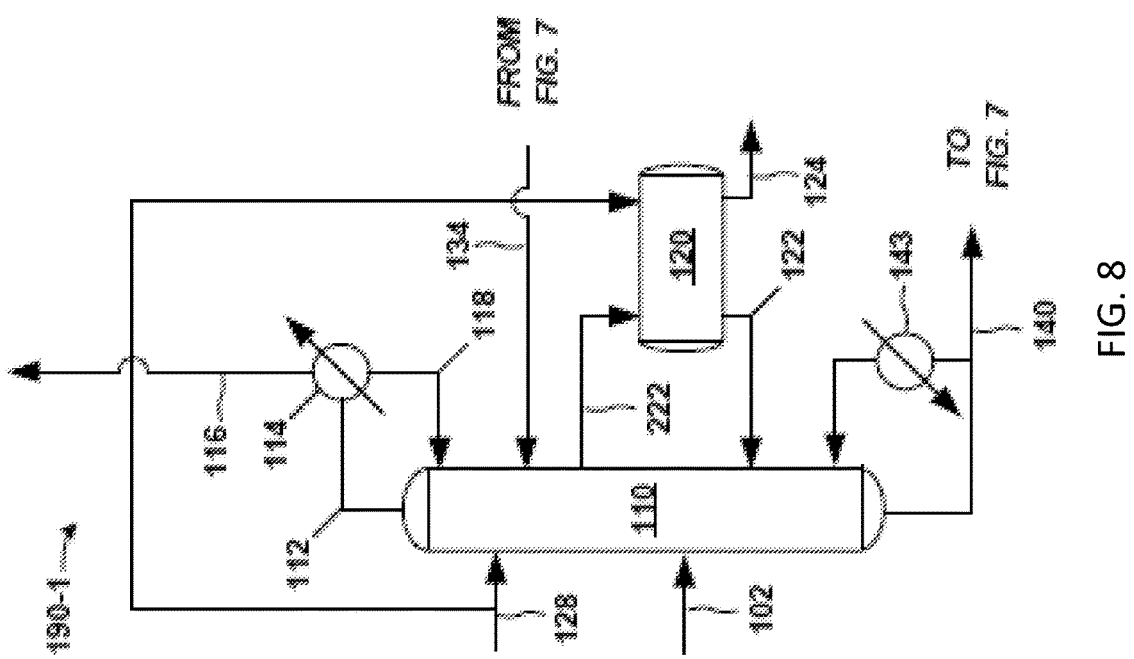
FIG. 8 is a schematic block diagram of an example of a solvent-lights column system of the front-end of FIG. 7 according to one embodiment.
Figure 9:
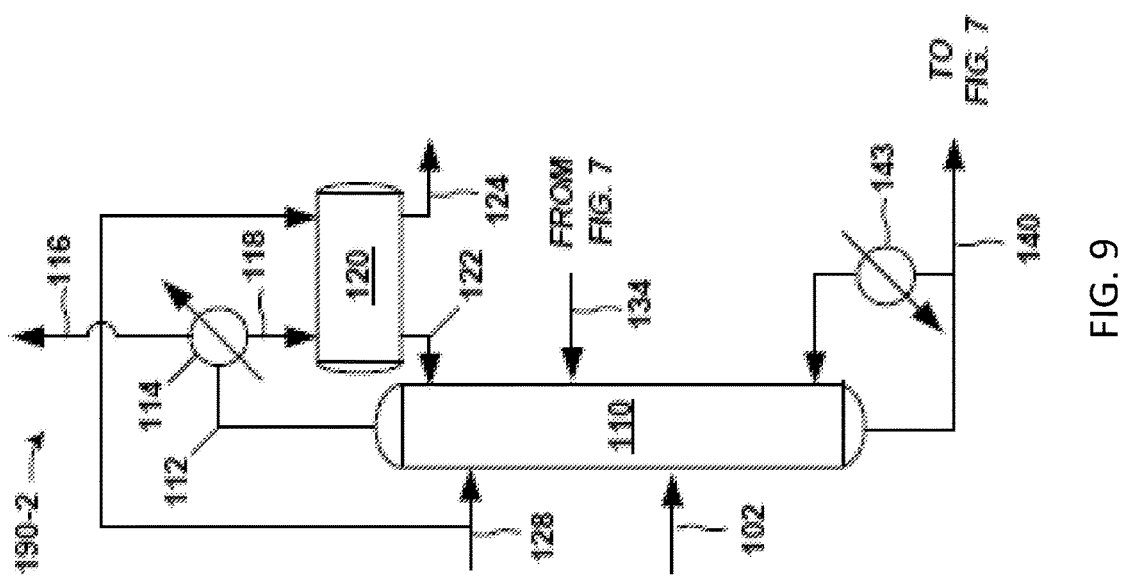
FIG. 9 is a schematic block diagram of another example of a solvent-lights column system of the front-end of FIG. 7 according to one embodiment.

A beneficial aspect of the solvent-lights column system 190 is the formation and discharge of the aqueous stream 124 having the aforementioned impurities, and which may be accomplished in a variety of configurations. FIGS. 8 and 9 provide respective examples of the solvent-lights column system 190 having the solvent-lights column 110 that gives aqueous stream 124 or a similar stream.

FIG. 8 is an exemplary solvent-lights column system 190-1 having the solvent-lights column 110 that receives the crude PO stream 102, which may be received at various distillation stages along the solvent-lights column 110. A solvent 128 is also fed to the column 110. In certain examples, it may be beneficial to introduce the solvent 128 at or above the liquid side draw 222. An exemplary introduction point for the solvent 128 is at stage or tray 3, for instance.

A decanter 120 is positioned as a side decanter to facilitate formation and discharge of the aqueous stream 124. A liquid side draw 222 from the solvent-lights column 110 having some PO and also having water, methanol, acetaldehyde, and other impurities from the solvent-lights column 110 is fed to the decanter 120. A purpose of the decanter 120 may be to facilitate removal of water and other aqueous or water-soluble impurities from the solvent-lights column 110 (via the aqueous stream 124 purge).

The liquid side draw 222 sent to the decanter 120 may have a relatively significant amount of water and other water-soluble impurities such as methanol. Thus, the decanter 120 may facilitate sufficient aqueous phase-out of the water and aqueous components on contact with hydrocarbon solvent. Therefore, solvent 128 (e.g., C8-C10) may be introduced to the decanter 120 to promote formation of an aqueous phase and an organic phase in the decanter 120. The organic phase in the decanter 120 gives the organic stream 122, which may be sent as reflux to the solvents-lights column 110.

The aqueous phase in the decanter 120 gives the aqueous stream 124, which is sent to the water wash system 126, as discussed (see FIG. 7). This aqueous stream 124 may contain PO and also water, methanol, acetaldehyde, some methyl formate, glycol and other impurities. At the water wash system 126, the aqueous stream 124 contacts additional hydrocarbon solvent (e.g., C8-C10) and a relatively small amount of water to promote the removal of water soluble impurities such methanol, acetaldehyde, glycol, a relatively small amount of methyl formate, and other impurities via the aqueous purge 130 (FIG. 7) from the water wash system 126. Propylene oxide (PO) is recovered in the solvent or organic phase returned in the wash organic stream 134 from the water wash system 126 (FIG. 7) to the solvent-lights column 110 shown in FIG. 8. This routing of the wash organic stream 134 is in contrast to the embodiment shown in FIG. 5, where the wash organic stream 134 from the water wash 126 is instead sent to the decanter 120, and where the organics and recovered PO reach the column 110 via organic stream 122 in FIG. 5.

In FIG. 8, an overhead stream 112, having light components, discharges from the solvent-lights column 110 and is partially condensed in an overhead condenser 114. In this example, the portion of the overhead stream 112 condensed is labeled as condensed overhead stream 118 which is returned as reflux to the solvent-lights column 110. A vapor stream 116 of non-condensed components is purged from the overhead condenser 114. In certain embodiments with respect to FIG. 8, operation of the overhead condenser 114 may be adjusted to give a vapor stream 116 purge in the range of 5-50 weight % range of the distillate (condensed overhead stream 118) to give 60-90 weight % (e.g., about 75 weight %) total methyl formate purge from the crude PO feed 102.

A product stream having a majority of the PO entering the solvent-lights column 110 in the crude PO stream 102 is discharged as a bottoms stream 140 from the solvent-lights column 110. As discussed with respect to FIG. 7, the product stream (bottoms stream 140) is sent as feed to the downstream solvent stripper 142 (see FIG. 7).

FIG. 9 reflects an exemplary solvent-lights column system 190-2 having the solvent-lights column 110 and a decanter 120 to facilitate formation and discharge of the aqueous stream 124. As similarly discussed with respect to FIG. 8, the solvent-lights column 110 in the solvent-lights column system 190-2 of FIG. 9 receives the crude PO stream 102. A solvent 128 is also fed to the column 110. In the example of FIG. 9, the decanter 120 is an overhead decanter and receives a condensed overhead stream 118 having the methanol, water, and other light aqueous impurities, instead of receiving a side draw 222 (FIG. 8) having such impurities from the column 110.

In FIG. 9, an overhead stream 112, having light components, discharges overhead from the solvent-lights column 110 and is partially condensed in an overhead condenser 114. In this example, the condensed overhead stream 118 is sent to the decanter 120.

A vapor stream 116 of non-condensed components is purged from the overhead condenser 114. In certain embodiments, operation of the overhead condenser 114 may be adjusted to give a vapor stream 116 purge in the range of 5-50 weight % range of the distillate and to give 60-90 weight % (e.g., about 75 weight %) total methyl formate purge from the crude PO feed 102.

As with system 190-1 (FIG. 8), solvent 128 may be introduced in the system 190-2 of FIG. 9 to the decanter 120 to facilitate formation of an aqueous phase and an organic phase in the decanter 120. In this illustrated example of FIG. 9, the organic stream 122 is returned as reflux to the column 110.

The aqueous phase discharges from the decanter 120 as aqueous stream 124 to the water wash system 126 (see FIG. 7). As with system 190-1, this aqueous stream 124 in system 190-2 generally contains PO and also water, methanol, acetaldehyde, some methyl formate, and other impurities. The aqueous stream 124 is sent to the water wash system 126, contacting additional hydrocarbon solvent (e.g., C8-C10) and a relatively small amount of water, for ultimate removal of water soluble impurities of methanol, acetaldehyde, glycol and a relatively small portion of methyl formate, and other impurities, via the downstream aqueous purge 130 (FIG. 7). PO is recovered in the returning of the wash organic stream 134 (PO and solvent) directly to the solvent-lights column 110 (not via the decanter 120 as in FIG. 8).

A product stream (bottoms stream 140) having a majority of the PO entering the solvent-lights column 110 in the crude PO stream 102 is discharged as bottoms stream 140 from the solvent-lights column 110. As discussed with respect to FIGS. 7 and 8, the product stream (bottoms stream 140) of FIG. 9 is sent as feed to the downstream solvent stripper 142 (see FIG. 7). Lastly, it is noted that other configurations of the lights-solvent column system 190 are contemplated to form and discharge the aqueous stream 124. In certain embodiments, a side cooler to the lights-solvent column 110, and/or other equipment may be employed, for example.

FIG. 10 is an exemplary back-end 106B of a separation system 100 (FIG. 4) associated with the front-end system 104B discussed above with respect to FIGS. 7-9. As with the back-end 106A of FIG. 6, the back-end 106B depicted in FIG. 10 includes an extraction column 160, solvent column 162, and PO column 164. For the sake of clarity, the respective reboilers for each column 160, 162, 164 are not shown, and the overhead condenser for the solvent column 162 is not depicted. The extraction column overhead condenser 240 for the extraction column 160 and the PO column overhead condenser 242 for the PO column 164 are shown.

For the primary feed to the extraction column 160, condensed overhead from the upstream stripper column 142 (FIG. 7) is sent as PO stream 108B to extraction column 160 for extraction with a solvent (e.g., C8-C10 hydrocarbon). A source of the solvent for the extraction may be the solvent bottoms stream 148 from the downstream solvent column 162. Of course, other sources of extraction solvent may be employed.

An extraction overhead stream 168 from the extraction column 160 is condensed in the extraction column overhead condenser 240, and a portion of the condensed extraction overhead stream 168 returned as reflux to the extraction column 160. Another portion of the condensed extraction overhead stream 168 is collected as distillate 199 and is sent to the upstream water wash system 126 (FIG. 7).

Advantageously, this purge of a portion of the condensed extraction overhead stream 168 collected as distillate 199 to the water wash system 126 generally contains formaldehyde, and thus reduces the amount of formaldehyde in the downstream PO column 164. Therefore, fouling of equipment associated with any overhead lights purge (not shown) from the PO column 164 may be reduced. The fouling may be due to formaldehyde polymer formation, for example.

In certain embodiments, with the purge of distillate 199 of the condensed extraction overhead stream 168 having the light component formaldehyde, the need for an overhead lights purge (such as the overhead lights purge 172 shown in FIG. 6) at the downstream PO column 164 may be eliminated, as depicted in FIG. 10. Further, the PO in the distillate 199 purge of condensed overhead stream 168 to the wash system 126 may be recovered in the wash organic stream 134 from the wash system 126 returned to the solvent-lights column 110 in the solvent-lights system 190 (see FIGS. 7-9). Moreover, the use of a PO product side draw (giving product side stream 248) in FIG. 10 reduces the amount of PO leaving in the distillate 199.

An extraction bottoms stream 170 having solvent and impurities discharges from the extraction column 160 and is fed to the solvent column 162. A hydrocarbon purge 178 (e.g., C6) is removed overhead and a solvent bottoms stream 148 is removed. As indicated, this solvent bottoms stream 148 may be fed to the extraction column 160. In addition, take-off portions of the solvent bottoms stream 148, such as recycle solvent 149 and back end solvent 151 in the illustrated embodiment of FIG. 10, may be sent to unit operations in the front-end 104B (see FIG. 7).

In this illustrated embodiment of FIG. 10, as indicated, a product side stream 248, having the majority of PO entering the extraction column 160, is discharged from the extraction column 160 to the PO column 164. This is in contrast to FIG. 6 where the product stream is the extraction overhead stream 168.

In the PO column 164 of FIG. 10, a bottoms heavies purge 174 is removed. A PO column overhead stream 252 discharges overhead and is condensed in the overhead condenser 242. An increased reflux rate of condensed PO column overhead stream 252 to the PO column 164 may reduce PO loss and beneficially increase separation of propionaldehyde and acetone from the PO in the PO column 164, for example. The condensed portion of PO column overhead stream 252 collected as product distillate is labeled as PO product stream 109B and may be analogous to the PO product stream 109 of FIG. 4.

In one example, a separation system 100 (FIG. 4) having the front-end 104B (FIGS. 7-9) and back-end 106B (FIG.

10) may give a relatively high yield of 98.5 weight % of PO recovery from the crude PO stream 102 in the condensed PO column overhead stream 252 sent as distillate product. In that example, the PO product stream 109B has high purity of 99.98 weight % PO with 10 ppm methyl formate. Lastly, it should be noted that the columns and associated equipment depicted in FIGS. 7-10 may be commercial scale, and have the sizing, internals, and materials of construction discussed above.

Figure 11:
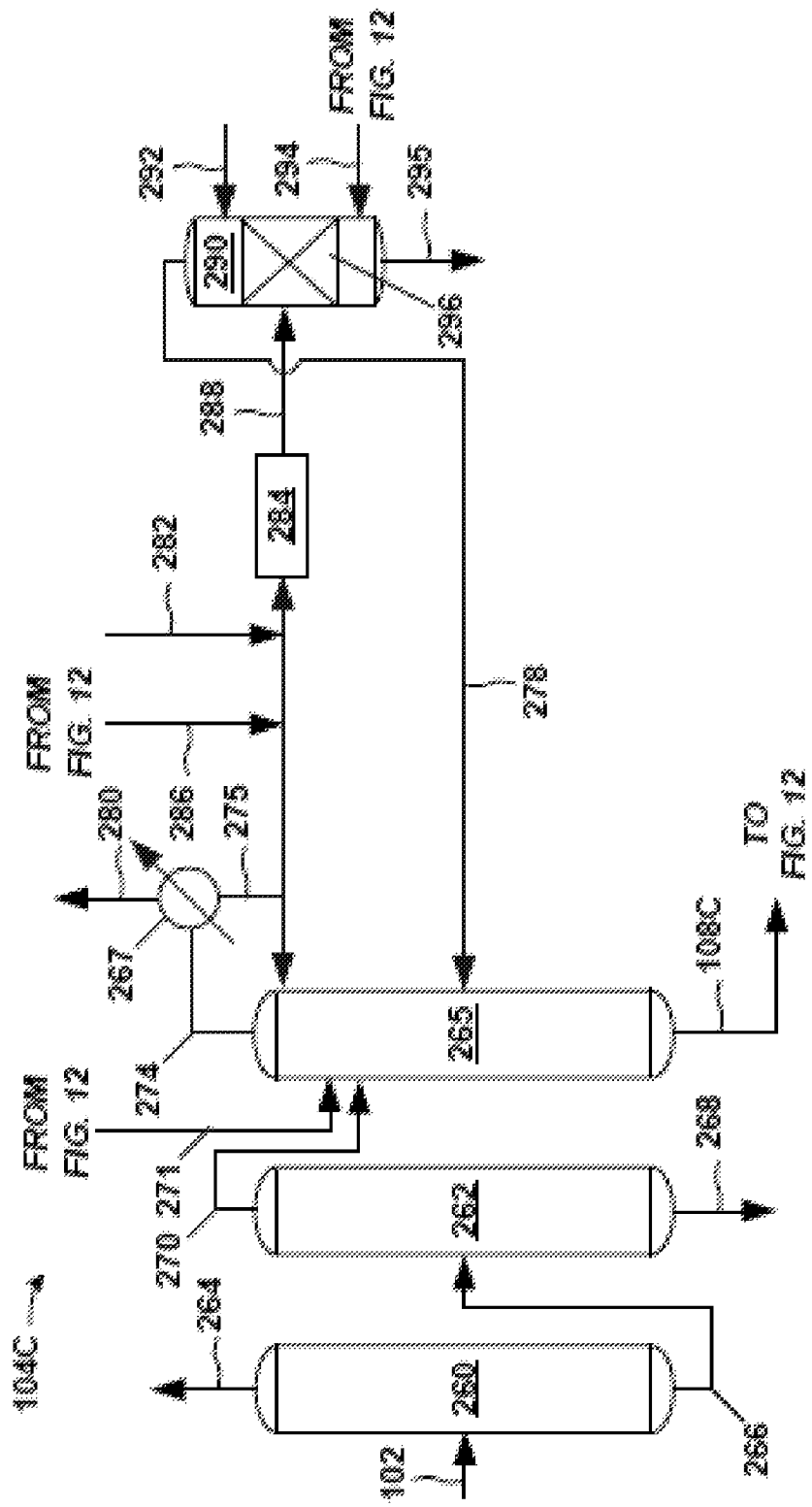
FIG. 11 is a schematic block diagram of yet another front-end of a propylene oxide separation system according to one embodiment.
Figure 12:
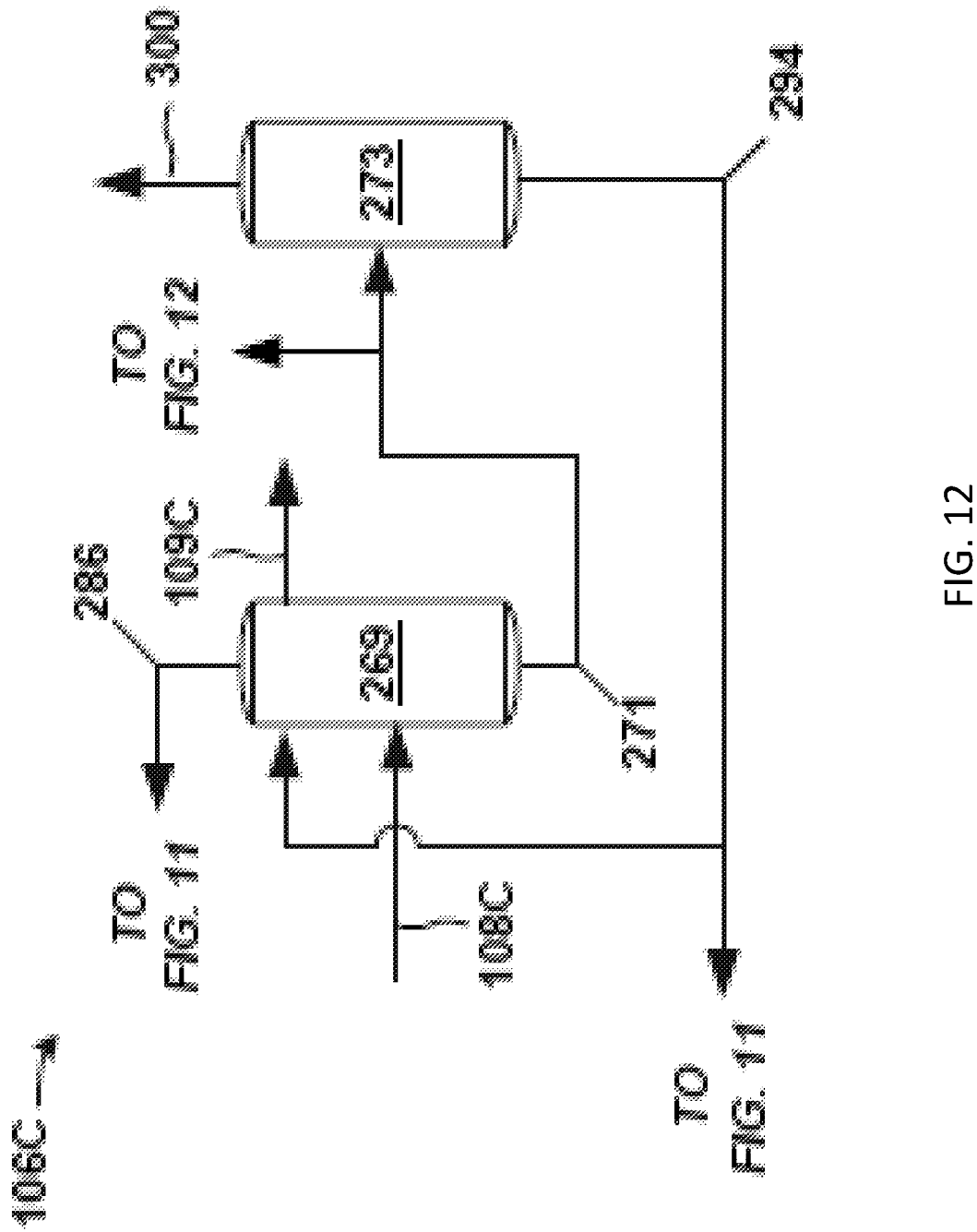
FIG. 12 is a schematic block diagram of a back-end of a propylene oxide separation system associated with the front-end of FIG. 11 according to one embodiment.

FIGS. 11 and 12 are an alternate embodiment for a front-end 104C and back-end 106C, respectively, of a separation system 100 (FIG. 4). The front-end 104C of FIG. 11 has a lights column 260, a heavies column 262, and a solvent-lights column 265 (e.g., with the column "solvent" as C8-C10s). These column 260, 262, and 265 may each be a distillation column. The associated back-end 106C of FIG. 12 has an extraction column 269 (or also labeled a solvent-heavies column) and a solvent column 273. In this embodiment, the PO product stream 109C (analogous to PO product stream 109 of FIG. 4) discharges from the extraction column 269. Moreover, a solvent purge (extraction overhead stream 286) is sent from the overhead of the extraction column 269 to the front-end 104C, thereby reducing the amount of the impurity formaldehyde in the extraction column 269 and PO product stream 109C.

For the sake of clarity, the respective reboilers and overhead condensers for each of the columns in FIGS. 11 and 12 are not depicted, except for the solvent-lights column overhead condenser 267 associated with the solvent-lights column 265. Moreover, the front-end 104C of FIG. 11 is depicted with the lights column 260 as receiving the crude PO stream 102 and feeding the heavies column 262. However, this process order within the front-end 104C may be altered (i.e., switched). In other words, the front-end 104C may be configured such that the heavies column 262 receives the crude PO stream 102 and feeds the lights column 260. In either case, the feed to the third column, the solvent-lights column 265, will typically be similar in composition and mass flow rate.

In the illustrated embodiment for the front-end 104C of FIG. 11, the crude PO stream 102 is fed to the lights column 260 for removal of light impurities and hydrocarbons, for example C5, via a lights column overhead stream 264. The lights column bottoms stream 266 from the lights column 260 contains most or a majority of the PO entering in the crude PO stream 102. This lights column bottoms stream 266 is fed to a heavies column 262 for removal of heavy components, water, some methanol, and the like, via a heavies column bottoms stream 268 from the heavies column 262. Examples of removed heavy components in the heavies column bottoms stream 268 can include propionaldehyde, acetone, and so forth.

The majority of the PO entering the heavies column 262 from the lights column 260 discharges in a heavies column overhead stream 270 (a product stream) from the heavies column 266. This heavies column overhead stream 270 has reduced methanol and water due to the presence of the upstream lights column 260. The heavies column overhead stream 270 is fed to the solvent-lights column 265. Further, a solvent (e.g., C6-C10s) is introduced to the solvent-lights column 265 via all or a portion of hydrocarbon bottoms stream 271 from the back-end 106C (FIG. 12). As discussed below, this hydrocarbon bottoms stream 271 has solvent recycled from the back-end 106C.

At the solvent-lights column 265, the solvent-lights column bottoms stream 108C is a product stream containing a majority of the PO entering the solvent-lights column 110 (in heavies column overhead stream 270) from the upstream heavies column 262. This solvent-lights column bottoms stream 108C may be analogous to the PO stream 108 of FIG. 4.

As for impurities, the light and aqueous impurities discharge overhead from the solvent-lights column 265 in an overhead stream 274. The overhead stream 274 is condensed in an overhead condenser 267 to give a condensed overhead stream 275. A vapor purge 280 from the overhead condenser 267 of about 5 to 10 weight %, for example, of the overhead stream 274 is maintained to remove some non-caustic and non-water soluble light components, and so forth. A portion of the condensed overhead stream 275 is refluxed to the solvent-lights column 265. The remaining portion of the condensed overhead stream 275 (i.e., distillate) is subjected to a caustic wash, as discussed below.

It should be noted that by operating the solvent-lights column 265 with sufficient solvent feed (e.g., via streams 270 and 271, and with targeted management of the condensed overhead stream 275 reflux and distillate, and so on, the light impurities of methyl formate, acetaldehyde, methanol, water, glycol, and the like, are generally concentrated in the condensed overhead stream 275 without an aqueous phase forming in the solvent-lights column 265 or in the condensed overhead stream 275.

As mentioned, the portion of the condensed overhead stream 275 not used as reflux but forwarded as distillate is sent to a caustic wash section and contacted with a slightly over-stoichiometric amount of caustic (e.g., sodium hydroxide), via caustic stream 282, equivalent to the amount of methyl formate in the portion of the condensed overhead stream 275 forwarded as distillate to maintain a pH of 10-12 in the caustic wash section in certain examples. In the illustrated embodiment, the caustic wash section is the addition of the caustic via caustic stream 282 and the mixer 284 that provides for mixing and residence time.

Further, a hydrocarbon solvent, such as an organic stream or solvent from the back-end 106C system, may be introduced upstream of the mixer 284, which may be, for example, a static mixer, to promote formation of an aqueous phase (i.e., having a majority of the water, methanol, acetaldehyde, methyl formate, and other water-soluble impurities, in the portion of the condensed overhead stream 275 forwarded as distillate to the caustic wash). The source of the solvent so added may be the extraction overhead stream 286 from the extraction column 269 in FIG. 12. Moreover, this extraction overhead stream 286 may contain formaldehyde and thus beneficially reduce formaldehyde in the back-end 106C and ultimately in the final PO product 109C. Furthermore, the PO in this extraction overhead stream 286 may be recovered in the recycle solvent stream 278 sent as reflux to the solvent-lights column 265.

The caustic-treated distillate 288 from the mixer 284 is fed to a backwash column 290 which may be a relatively small PO wash/recovery, liquid-liquid extraction column having about 3-7 (e.g., 5) theoretical stages satisfied via packing 296, for example, and generally in a middle portion of the column, for instance. Water 292 is introduced at a top portion and solvent 294 introduced at a bottom portion of the backwash column 290. The extraction in the backwash column 290 increases PO recovery from the caustic/water waste in the caustic-treated distillate 288 with reduced caustic carryover at reduced aqueous phase. In this example, the caustic/water waste 295 discharges from a bottom portion of the backwash column 290. The backwashed PO is returned to the solvent-lights column 265 in an organic stream (recycle solvent stream 278) as additional reflux for the column 265. Lastly, the solvent 294 fed to the backwash column 290 is a solvent (e.g., C8-C10s) from the back-end 106C system (FIG. 12).

As discussed, FIG. 12 is the exemplary back-end 106C associated with the exemplary front-end 104C (FIG. 11) of an exemplary separation system 100 (FIG. 4). Referring to FIG. 12, the extraction column 269 receives as feed the product stream (solvent-lights column bottoms stream 108C) from the solvent-lights column 265 (FIG. 11). Further, the extraction column 269 receives solvent 294 (e.g., C8-C10s) from a bottoms stream discharging from the downstream solvent column 273.

A condensed extraction overhead stream 286 (condenser not shown) from the extraction column 269 is sent to the caustic wash section (mixer 284, optionally a static mixer) of the front-end 104C (FIG. 11). The extraction overhead stream 286 may generally have hydrocarbon solvent, formaldehyde, PO, and so on. The hydrocarbon solvent in extraction overhead stream 286 may promote aqueous phase formation and separation in the backwash column 290 (FIG. 11). Further, the PO (e.g., 1-2 weight % based on the PO in the crude PO stream 102) sent in extraction overhead stream 286 to the caustic wash (in mixer 284) and the backwash column 290 may be recovered in the organic phase stream (recycle solvent stream 278) sent as reflux to the solvent-lights column 265 (FIG. 11). Lastly, as discussed, this purging of formaldehyde with the extraction overhead stream 286 may reduce the amount of formaldehyde in the extraction column 269 and in the PO product stream 109C discharging as a side draw from the extraction column 269.

Furthermore, a hydrocarbon bottoms stream 271, having heavy hydrocarbon solvent (e.g., C6-C10s), for example, discharges from the extraction column 269 and is fed to the solvent column 273. Moreover, a portion of this hydrocarbon bottoms stream 271 (e.g., having C6-C10s) may be fed to the solvent-lights column 265 (FIG. 11). At the solvent column 273, a hydrocarbon purge 300 (e.g., having C6) is taken overhead. A solvent stream 294 (e.g., having C8-C10s) discharges from the bottom of the solvent column 273 and may be sent to the extraction column 269 for the extraction, and/or sent for the liquid-liquid extraction in the backwash column 290 (FIG. 11).

Lastly, as indicated, the PO product stream 109C is recovered in a side draw (e.g., from the pasteurization section) of the extraction column 269. In sum, an exemplary PO separation system 100 having the front-end 104C and back-end 106C may provide an exemplary high yield of 98.9 weight % (of the PO in the crude PO stream 102), for example, and an exemplary high purity of 99.99 weight % PO with 10 ppm methyl formate in the PO product 109C.

The equipment depicted in FIGS. 11 and 12 may be commercial scale. Further, the respective diameters, heights, and the numbers of theoretical stages of the various columns in FIGS. 11 and 12 may be sized as a function of the design basis for the mass flow rate and composition of the incoming crude PO stream 102, for instance. To provide for the theoretical stages, trays or packing may be employed. Trays may include sieve trays, bubble cap trays or valve trays, and the like. The packing, which may be structured or dumped, can be glass, metal, plastic, and ceramic, and so on. The metallurgy or materials of construction of the various equipment in FIGS. 11 and 12 may include carbon steel, stainless steel, fiberglass reinforced polymer (FRP), nickel alloys, and so on.

In summary, embodiments of the present techniques may provide for a propylene oxide separation system including a distillation column to receive a crude propylene oxide stream, discharge an impurity stream having methanol and water, and discharge a bottoms stream having a majority of the propylene oxide entering in the crude propylene oxide stream. A decanter may receive the impurity stream and a hydrocarbon solvent to provide for formation in the decanter of an organic phase including propylene oxide and hydrocarbon solvent, and an aqueous phase including a majority weight percent of the methanol and the water entering in the impurity stream. A water wash system receives and purges the aqueous phase from the propylene oxide separation system, wherein the organic phase in the decanter is sent to the distillation column. The crude propylene oxide stream may be a propylene oxide reactor effluent stream, such as in a propylene oxide/tert-Butanol process system.

The distillation column may include an overhead condenser, and wherein the distillation column is configured with an overhead vapor purge of non-condensed components from the overhead condenser. The decanter may be an overhead decanter to the distillation column, and receive the impurity stream from the overhead condenser. On the other hand, the decanter is a side decanter to the distillation column, and is configured to receive the impurity stream from a liquid side draw of the distillation column. The distillation column may be a solvent-lights column. Further, the water wash system may include a static mixer and a coalescer. A solvent stripper may receive the bottoms stream from the distillation column, wherein the solvent stripper discharges a solvent-stripper overhead stream having a majority of the propylene oxide entering the solvent stripper in the bottoms stream from the distillation column, and wherein the solvent stripper discharges a solvent-stripper bottoms stream having at least a portion of the hydrocarbon solvent received at the decanter. Lastly, an extraction column may subject the solvent-stripper overhead stream from the solvent stripper to a hydrocarbon solvent extraction to remove impurities, wherein the extraction column purges the removed impurities including formaldehyde to the water wash system.

Embodiments may provide for a method of separating propylene oxide from a crude propylene oxide stream in a separation system, the method including: feeding the crude propylene oxide stream to a distillation column; discharging an impurity stream from the distillation column to a decanter, the impurity stream comprising methanol and water; feeding hydrocarbon solvent to the decanter; and forming in the decanter an organic phase comprising propylene oxide and hydrocarbon solvent, and an aqueous phase comprising a majority weight percent of the methanol and the water fed to the decanter in the impurity stream. Further, the method may include washing the aqueous phase with water and purging the washed aqueous phase from the separation system, and sending the organic phase to the distillation column.

The discharging of the impurity stream may include discharging the impurity stream to the decanter via an overhead condenser of the distillation column, and the method further including purging a vapor stream from the overhead condenser. On the other hand, the discharging the impurity stream may involve discharging the impurity stream to the decanter via a liquid side draw of the distillation column. Lastly, the method may include: discharging a bottoms stream from the distillation column, the bottoms stream comprising a majority of the propylene oxide entering the distillation column in the crude propylene oxide stream; separating formaldehyde from the bottoms stream; and sending the formaldehyde to a water wash system performing the washing of the aqueous phase with water.

Certain embodiments may include a propylene oxide separation system having a distillation column to receive a processed crude propylene oxide stream, discharge an impurity stream comprising methanol and water, and discharge a bottoms stream having a majority of the propylene oxide entering in the processed crude propylene oxide stream. A mixer mixes caustic (e.g., having sodium hydroxide) with the impurity stream to give a caustic-treated impurity stream. A backwash column subjects the caustic-treated impurity stream to both an aqueous extraction and an organic extraction. The backwash column may purge an aqueous stream having a majority amount of the methanol and the water in the impurity stream. In addition, the backwash column may discharge an organic stream (having hydrocarbon solvent and propylene oxide) to the distillation column. The propylene oxide separation system may include an extraction column disposed downstream of the distillation column, and configured to purge formaldehyde to the mixer, wherein the formaldehyde is carryover from the bottoms stream of the distillation column.

Lastly, some embodiments may include a method for separating impurities from propylene oxide, the method including processing via a distillation column a propylene oxide stream to discharge an impurity stream having methanol and water, and to discharge a bottoms stream having a majority of the propylene oxide entering the distillation column. The impurity stream is mixed (e.g., via a static mixer) with caustic (e.g., having sodium hydroxide) to give a caustic-treated impurity stream which is then extracted with hydrocarbon, and then extracted with water to purge an aqueous stream having a majority of the methanol and water in the impurity stream. The method may include processing the bottoms stream from the distillation column and purging formaldehyde via the processing to the impurity stream.

Although the present invention has been described in considerable detail with reference to certain preferred versions thereof, other versions are possible. Therefore, the spirit and scope of the appended claims should not be limited to the description of the preferred versions contained herein.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means for" performing a specified function, or "step for" performing a specific function, is not to be interpreted as a "means" or "step" clause as specified in 35 U.S.C § 112, sixth paragraph. In particular, the use of "step of" in the claims herein is not intended to invoke the provisions of 35 U.S.C § 112, sixth paragraph.

What is claimed is:

1. A method for separating propylene oxide from a crude propylene oxide stream in a separation system, the method comprising:
    feeding the crude propylene oxide stream to a distillation column;
    discharging an impurity stream from the distillation column to a decanter, the impurity stream comprising methanol and water;
    discharging a bottoms stream from the distillation column to a solvent stripper, the bottoms stream comprising propylene oxide;
    feeding hydrocarbon solvent to the decanter;
    forming in the decanter an organic phase comprising propylene oxide and hydrocarbon solvent, and an aqueous phase comprising a majority weight percent of the methanol and the water fed to the decanter in the impurity stream;
    washing the aqueous phase with water and purging the washed aqueous phase from the separation system;
    sending the organic phase to the distillation column;
    discharging an overhead stream from the solvent stripper to an extraction column, the overhead stream from the solvent stripper comprises a majority of propylene oxide; and
    removing impurities from the overhead stream from the solvent stripper in the extraction column, wherein the removed impurities comprise one or more of formaldehyde, methyl formate, acetaldehyde and methanol and wherein the extraction column purges the removed impurities to a water wash system.

2. The method of claim 1, wherein discharging the impurity stream comprises discharging the impurity stream to the decanter via an overhead condenser of the distillation column, and the method further comprises purging a vapor stream from the overhead condenser.

3. The method of claim 1, wherein discharging the impurity stream comprises discharging the impurity stream to the decanter via a liquid side draw of the distillation column.

4. The method of claim 1, comprising:
    separating formaldehyde from the bottoms stream in the solvent stripper; and
    sending the formaldehyde to a water wash system performing the washing of the aqueous phase with water.

* * * * *